US009778209B2

United States Patent
Nishimura et al.

(10) Patent No.: US 9,778,209 B2
(45) Date of Patent: Oct. 3, 2017

(54) SUBSTRATE FOR MASK BLANKS, MASK BLANK, TRANSFER MASK, AND METHOD OF MANUFACTURING THEM

(71) Applicant: HOYA CORPORATION, Tokyo (JP)

(72) Inventors: Takahito Nishimura, Tokyo (JP); Kazuki Aoyama, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 15/122,484

(22) PCT Filed: Dec. 9, 2014

(86) PCT No.: PCT/JP2014/082481
§ 371 (c)(1),
(2) Date: Aug. 30, 2016

(87) PCT Pub. No.: WO2015/145887
PCT Pub. Date: Oct. 1, 2015

(65) Prior Publication Data
US 2017/0074807 A1  Mar. 16, 2017

(30) Foreign Application Priority Data
Mar. 26, 2014 (JP) .................. 2014-063308

(51) Int. Cl.
*G01N 21/00* (2006.01)
*G01N 21/956* (2006.01)
(Continued)

(52) U.S. Cl.
CPC ............ *G01N 21/956* (2013.01); *G03F 1/60* (2013.01); *G03F 1/84* (2013.01); *G01N 2021/95676* (2013.01)

(58) Field of Classification Search
CPC ........ G01N 21/956; G01N 2021/95676; G03F 1/84; G03F 1/60; G03F 1/22; G03F 7/20; G02B 5/08; G03B 27/72
See application file for complete search history.

(56) References Cited

U.S. PATENT DOCUMENTS

2002/0162979 A1  11/2002  Kusunose
2005/0197242 A1   9/2005  Mitra et al.
(Continued)

FOREIGN PATENT DOCUMENTS

JP          64-40267 A     2/1989
JP        2001-27611 A     1/2001
(Continued)

OTHER PUBLICATIONS

International Search Report for PCT/JP2014/ dated Mar. 17, 2015 [PCT/ISA/210].

*Primary Examiner* — Jamil Ahmed
(74) *Attorney, Agent, or Firm* — Sughrue Mion, PLLC

(57) ABSTRACT

Provided is a mask blank substrate being a substrate having two main surfaces, in which one of the two main surfaces of the mask blank substrate on a side on which a transfer pattern is formed has such a surface profile that, when a measurement region of 2.8 mm×2.1 mm of the main surface in a transfer pattern formation region is measured using a white light interferometer under conditions of a pixel number of 640×480, a power spectrum density at a spatial frequency of $1.0\times10^{-2}$ $\mu m^{-1}$ calculated from a result of the measurement is $6.0\times10^{7}$ $nm^{4}$ or less.

13 Claims, 5 Drawing Sheets

(51) Int. Cl.
    *G03F 1/60*    (2012.01)
    *G03F 1/84*    (2012.01)

(56)        References Cited

U.S. PATENT DOCUMENTS

2006/0132749 A1*  6/2006  Bruls .................. G03F 7/70433
                                                         355/69
2008/0123086 A1   5/2008  Kudo et al.
2015/0017574 A1   1/2015  Orihara et al.

FOREIGN PATENT DOCUMENTS

JP      2002-328099 A    11/2002
JP      2005-231994 A     9/2005
JP      2006-176341 A     7/2006
JP       2008-94649 A     4/2008
JP       2013-61239 A     4/2013
WO      2006/030684 A1    3/2006
WO      2013/146990 A1   10/2013

* cited by examiner

SUBSTRATE FOR MASK BLANKS, MASK BLANK, TRANSFER MASK, AND METHOD OF MANUFACTURING THEM

CROSS REFERENCE TO RELATED APPLICATIONS

This application is a National Stage of International Application No. PCT/JP2014/082481, filed on Dec. 9, 2014, which claims priority from Japanese Patent Application No. 2014-063308, filed on Mar. 26, 2014, the contents of all of which are incorporated herein by reference in their entirety.

TECHNICAL FIELD

This invention relates to a mask blank substrate that may suppress detection of a false defect due to surface roughness of the substrate in defect inspection using a highly sensitive defect inspection apparatus and may facilitate finding of a fatal defect such as a foreign matter or a flaw, a mask blank, and a transfer mask obtained from the mask blank substrate, and to methods of manufacturing the mask blank substrate, the mask blank, and the transfer mask.

BACKGROUND ART

In general, in a manufacturing process of a semiconductor device, a fine pattern is formed using photolithography. Further, the fine pattern is typically formed using a plurality of transfer masks that are called photomasks. This transfer mask is generally a transparent glass substrate having a fine pattern, which is formed of a metal thin film or the like, formed on a main surface thereof. Also in manufacturing the transfer masks, photolithography is used.

In manufacturing a transfer mask using photolithography, a mask blank having a thin film (for example, a light-shielding film) for forming a transfer pattern (mask patter) on a transparent substrate such as a glass substrate is used. The manufacturing of a transfer mask using a mask blank has a drawing step of drawing a desired pattern on a resist film formed on the mask blank, a developing step of developing, after the drawing, the resist film to form a desired resist pattern, an etching step for forming the thin film with the resist pattern being used as a mask, and a step of separating and removing a remaining resist pattern. In the developing step, after the desired pattern is drawn on the resist film formed on the mask blank, a developer is supplied to dissolve a portion of the resist film soluble in the developer, thereby forming the resist pattern. Further, in the etching step, an exposed portion of the thin film on which no resist pattern is formed is removed by dry etching or wet etching with the resist pattern being used as a mask, thereby forming the desired mask pattern on the transparent substrate. In this way, the transfer mask may be manufactured.

As kinds of the transfer mask, other than a related-art binary type mask having a light-shielding film pattern formed of a chromium-based material on a transparent substrate, a phase shift type mask (also simply referred to as "phase shift mask") is known. The phase shift type mask has a structure including a phase shift film on a transparent substrate. The phase shift film causes a predetermined phase difference with respect to exposure light, and, for example, a material containing a molybdenum silicide compound is used. Further, a binary type mask in which a material containing a silicide compound of a metal such as molybdenum is used as a light-shielding film is also coming into general use. These binary type masks and phase shift type masks are herein collectively referred to as transmission type masks. Further, binary type mask blanks and phase shift type mask blanks serving as originals used for transmission type masks are collectively referred to as transmission type mask blanks.

As described above, increasing demand for forming finer patterns in a lithography step causes problems in the lithography step to be noticeable. One of the problems relates to defect information on a mask blank substrate used in the lithography step.

As the mask blank substrate, from the viewpoint of improvement in defect quality accompanying finer patterns in recent years and of optical characteristics required for the transfer mask, a smoother substrate is required.

As a typical method of manufacturing precision polished glass, for example, there is described in JP-A-S64-40267 (Patent Document 1) a method of manufacturing precision polished glass in which, after a glass surface is polished using a polishing material with cerium oxide being a main material thereof, polish finishing is given using colloidal silica.

A mask blank to be an original of a transfer mask used in photolithography is produced by forming, on a substrate of synthetic quartz glass or the like, a thin film for pattern formation by sputtering. A substrate used for a mask blank is required to have no defect on a main surface thereof, or, if there are some, the number of the defects is required to be a predetermined number or less. Therefore, defect inspection is generally made to the main surface of the substrate using a defect inspection apparatus as disclosed in JP-A-2001-027611 (Patent Document 2) and JP-A-2002-328099 (Patent Document 3), thereby inspecting whether or not there is a defect on the main surface or the like.

PRIOR ART DOCUMENTS

Patent Document

Patent Document 1: JP-A-S64-40267
Patent Document 2: JP-A-2001-027611
Patent Document 3: JP-A-2002-328099

SUMMARY OF THE INVENTION

Problem to be Solved by the Invention

In defect inspection made to a main surface of a mask blank substrate or a surface of a thin film of a mask blank, mainly two inspection methods are used. One inspection method is an inspection method as disclosed in Patent Document 2 in which two polarized beams coherent to each other are radiated to the main surface of the substrate, and whether or not there is a defect and the kind of the defect (recess defect, protrusion defect, or the like) are determined by interference with reflected light or the like (two beam interference method). Another inspection method is an inspection method as disclosed in Patent Document 3 in which whether or not there is a detect on the main surface of the substrate and the kind of the defect (recess defect, protrusion defect, or the like) are determined by an optical system in which a spatial filter, e.g., a knife-edge filter is incorporated in a confocal optical system (spatial filter method).

A method of using a defect inspection apparatus disclosed in Patent Document 2 is an example of a defect inspection method as the two beam interference method. Specifically, the defect inspection method as the two beam interference method disclosed in Patent Document 2 is as follows. In the defect inspection method as the two beam interference method, a light beam emitted from a light source device is converted into two sub-beams coherent to each other by a coherent optical system. These sub-beams scan a sample surface to which the defect inspection is to be made. When there is a defect on the sample surface, one of the two sub-beams scans the defect portion and another scans a normal portion adjacent to the defect, and thus, a phase difference corresponding to a size of the defect in a height direction is caused between the sub-beams. The relationship between the amplitude of an interference beam obtained by synthesizing the sub-beams reflected by the sample surface by the coherent optical system and the phase difference between the sub-beams is that, when the phase difference between the two sub-beams changes from 0 to $\pi$ (corresponding to ¼ wavelengths), the amplitude of the interference beam changes from the sum of those of the two sub-beams to 0. Through using this relationship, a defect detection apparatus having extremely high detection sensitivity to a minute defect may be realized because the amplitude of the interference beam, i.e., brightness information, changes from a normal value to almost zero. In addition, through two-dimensional scanning of the sample surface with a plurality of light beams, the defect detection may be made at high speed.

A method of using a defect inspection apparatus disclosed in Patent Document 3 is an example of a defect inspection method as the spatial filter method. Specifically, the defect inspection method as the spatial filter method disclosed in Patent Document 3 is as follows. In the defect inspection method as the spatial filter method, a radiation beam emitted from a light source is converted into a light beam array arranged in a matrix of m×n by a diffraction grating. These light beams are focused into a beam spot by an objective lens to form a light spot array in a matrix of m rows and n columns on a sample to which the defect inspection is to be made. The sample to which the defect inspection is to be made is supported on a sample stage, and the sample stage is rotationally moved or translationally moved along a radial direction orthogonal to a rotation axis. In this way, m×n light spots scan the sample to be inspected, and the sample surface is scanned by a wide swath of m×n light beams. As a result, the sample surface may be scanned at high speed, and inspection time may be greatly reduced. Further, in a defect inspection method as the spatial filter method, a photodetector includes an array of light-receiving elements that are two dimensionally arranged in a matrix and are separated from one another by a light-shielding member, and thus, an optical system in this defect inspection method forms a confocal optical system. As a result, flare light due to a minute level difference and unevenness existing on the sample surface is prevented from entering the light-receiving elements, and only regularly reflected light from the light spots formed on the sample surface enter the light-receiving elements. Therefore, the influence of the flare may be removed to realize an optical system having high resolution. As a result, in the defect inspection method as the spatial filter method, a defect inspection apparatus that greatly reduces the inspection time and that has extremely high resolution may be realized.

In recent years, when a transfer pattern (when a light-shielding film is patterned, referred to as "light-shielding film pattern") formed on a transfer mask is becoming finer and finer. With that, an upper limit of the size of a defect permitted to exist on the main surface of a mask blank substrate is becoming smaller. In general, an inspection method as the spatial filter method has higher resolution of detecting a defect on a main surface of a substrate. Therefore, in recent years, defect inspection of a main surface of a substrate is made with a defect inspection apparatus of the spatial filter method more often than before.

Meanwhile, a defect inspection apparatus of the spatial filter method has a problem in that time necessary for the inspection is longer than that of a defect inspection apparatus of the two beam interference method. Therefore, in defect inspection of a mask blank substrate in which the upper limit of a permitted defect size is relatively large, a defect inspection apparatus of the two beam interference method tends to be used. Further, in order to increase throughput of the defect inspection, substrates for mask blanks are selected in a two-stage defect inspection step. In this case, first, primary defect inspection of the substrate is made by a defect inspection apparatus of the two beam interference method, and only a substrate without a defect of a relatively large size is selected. Then, secondary defect inspection is made by a defect inspection apparatus of the spatial filter method with regard to a substrate selected as a result of the primary defect inspection, and a substrate without a defect of a predetermined size or larger is selected as a mask blank substrate.

Further, in general, a defect inspection method as the two beam interference method is, in the case of, for example, a protrusion defect, excellent in detecting a gentle hill-like defect existing on a surface to be measured. On the other hand, a defect inspection method as the spatial filter method is, in the case of, for example, a protrusion defect, excellent in detecting a defect having a steep side wall. In order to produce a transmission type transfer mask with a high yield, in defect inspection of main surfaces of a mask blank substrate, a mask blank, and a transfer mask, it is necessary to make defect inspection using defect inspection methods of the two types, i.e., both the defect inspection method as the two beam interference method and the defect inspection method as the spatial filter method.

In general, in defect inspection of a substrate, it is known that a phenomenon occurs in which, even when a defect inspection apparatus determines that there is a defect on a main surface of a substrate, no defect actually exists at a predetermined position on the main surface at which the defect is determined to exist. A defect erroneously detected in this way is called a false defect. There are various reasons that a false defect is detected depending on the inspection conditions. Thus, appropriate solution measures are generally taken for the respective details of the false defect.

The inventors of this invention have made it clear that, in a plurality of substrates having different main surface geometries, when defect inspection of main surfaces of the substrates is made by a defect inspection apparatus of the spatial filter method, there may be no remarkable difference in the number of detected false defects among the substrates, while, when defect inspection is made by a defect inspection apparatus of the two beam interference method, there may be remarkable difference in the number of detected false defects among the substrates. When defect inspection of a substrate in which such a phenomenon occurs is made by a defect inspection apparatus of the two beam interference method, even when the substrate may be actually used as a mask blank substrate, it is erroneously determined that the substrate is a substrate having a large number of defects thereon, which is a problem. For the purpose of contrasting an actually existing defect with a false defect, the former is herein referred to as a real defect.

Accordingly, it is an object of this invention to obtain a mask blank substrate and a manufacturing method thereof that may, even when defect inspection of main surfaces of substrates is made using a defect inspection apparatus of the two beam interference method, suppress remarkable difference from being made in the number of detected false defects among the substrates. It is another object of this invention to obtain a mask blank, a transfer mask, and manufacturing methods thereof that can, even when defect inspection of main surfaces of mask blanks or transfer masks is made using a defect inspection apparatus of the two beam interference method, suppress remarkable difference from being made in the number of detected false defects among the mask blanks or the transfer masks.

Means to Solve the Problem

As a result of diligent effort and review for the purpose of solving the problem described above, the inventors of this invention have found a relationship between roughness of a predetermined spatial frequency (or spatial wavelength) component for a wavelength of an inspection light source of a defect inspection apparatus of the two beam interference method and the number of detected defects including false defects. Accordingly, the inventors of this invention have found that, through specifying a spatial frequency of a roughness component that a defect inspection apparatus of the two beam interference method erroneously determines to be a false defect among roughness (unevenness) components on a main surface of a substrate, and controlling amplitude intensity (power spectrum density) at the spatial frequency, the number of detected defects including false defects in defect inspection using the two beam interference method may be reduced, to thereby reach this invention.

Specifically, this invention is a mask blank substrate having Configurations 1 to 4 described below, a mask blank having Configuration 5 described below, and a transfer mask having Configuration 6 described below. Further, this invention is a method of manufacturing a mask blank substrate having Configurations 7 to 11 described below, a method of manufacturing a mask blank having Configuration 12 described below, and a method of manufacturing a transfer mask having Configuration 13 described below.

(Configuration 1)

Configuration 1 of this invention is a mask blank substrate, comprising a substrate having two main surfaces, wherein one of the two main surfaces of the mask blank substrate, on a side on which a transfer pattern is formed, has such a surface profile that, when a measurement region of 2.8 mm×2.1 mm of the main surface in a transfer pattern formation region is measured using a white light interferometer under conditions of a pixel number of 640×480, a power spectrum density at a spatial frequency of $1.0 \times 10^{-2}$ $\mu m^{-1}$ calculated from a result of the measurement is $6.0 \times 10^{7}$ $nm^4$ or less.

According to Configuration 1 described above, the main surface of the mask blank substrate, on a side on which a transfer pattern is formed, has such a surface profile that, when a measurement region of 2.8 mm×2.1 mm of the main surface in a transfer pattern formation region is measured using a white light interferometer with a pixel number of 640×480, a power spectrum density at a spatial frequency of $1.0 \times 10^{-2}$ $\mu m^{-1}$ calculated from a result of the measurement is $6.0 \times 10^{7}$ $nm^4$ or less. With this configuration, detection of a false defect may be suppressed when defect inspection of a mask blank substrate is made using the defect inspection apparatus of the two beam interference method, which may clarify a fatal defect.

(Configuration 2)

Configuration 2 of this invention is a mask blank substrate according to Configuration 1, wherein the main surface on the side on which the transfer pattern is formed has such a surface profile that, when a measurement region of 693 $\mu m \times 520$ $\mu m$ of the main surface in the transfer pattern formation region is measured using the white light interferometer under conditions of a pixel number of 640×480, a power spectrum density at a spatial frequency of $5.0 \times 10^{-2}$ $\mu m^{-1}$ calculated from a result of the measurement is $3.0 \times 10^{5}$ $nm^4$ or less.

According to Configuration 2 of this invention, detection of a false defect may be further suppressed when defect inspection of a mask blank substrate is made using the defect inspection apparatus of the two beam interference method, which may further clarify a fatal defect.

(Configuration 3)

Configuration 3 of this invention is a mask blank substrate according to Configuration 1 or 2, wherein the main surface on the side on which the transfer pattern is formed has a such surface profile that, when a measurement region of 140 $\mu m \times 105$ $\mu m$ of the main surface in the transfer pattern formation region is measured using the white light interferometer under conditions of a pixel number of 640×480, a power spectrum density at a spatial frequency of $2.0 \times 10^{-1}$ $\mu m^{-1}$ calculated from a result of the measurement is $8.0 \times 10^{2}$ $nm^4$ or less.

According to Configuration 3 of this invention, detection of a false defect may be suppressed even further when defect inspection of a mask blank substrate is made using the defect inspection apparatus of the two beam interference method, which may clarify a fatal defect even further.

(Configuration 4)

Configuration 4 of this invention is a mask blank substrate according to any one of Configurations 1 to 3, wherein the main surface on a side different from the side on which the transfer pattern is formed has such a surface profile that, when a measurement region of 2.8 mm×2.1 mm of the main surface in a region having the same size as the transfer pattern formation region is measured using the white light interferometer under conditions of a pixel number of 640×480, a power spectrum density at a spatial frequency of $1.0 \times 10^{-2}$ $\mu m^{-1}$ calculated from a result of the measurement is $6.0 \times 10^{7}$ $nm^4$ or less.

According to Configuration 4 of this invention, detection of a false defect may be suppressed also when defect inspection of a mask blank substrate is made using the defect inspection apparatus of the two beam interference method with regard to a main surface on a side different from a side on which the transfer pattern is formed, which may clarify a fatal defect.

(Configuration 5)

Configuration 5 of this invention is a mask blank, comprising a thin film for forming the transfer pattern formed on the main surface of the mask blank substrate of any one of Configurations 1 to 4 on the side on which the transfer pattern is formed.

According to Configuration 5 of this invention, detection of a false defect may be suppressed when defect inspection of a thin film for forming a transfer pattern of a mask blank is made using the defect inspection apparatus of the two beam interference method through use of the mask blank substrate with a main surface having a predetermined surface profile, which may clarify a fatal defect existing on the mask blank.

(Configuration 6)

Configuration 6 of this invention is a transfer mask, comprising the thin film of the mask blank of Configuration 5, which has the transfer pattern formed thereon.

According to Configuration 6 of this invention, detection of a false defect may be suppressed when defect inspection of a transfer mask is made using the defect inspection apparatus of the two beam interference method, which may clarify a fatal defect existing on the transfer mask.

(Configuration 7)

Configuration 7 of this invention is a method of manufacturing a mask blank substrate comprising a substrate having two main surfaces, the method comprising a defect inspection step of making defect inspection using a two beam interference method with regard to one of the two main surfaces of the mask blank substrate on a side on which a transfer pattern is formed and in a transfer pattern formation region, wherein the main surface of the mask blank substrate on the side on which the transfer pattern is formed has such a surface profile that, when a measurement region of 2.8 mm×2.1 mm of the main surface in the transfer pattern formation region is measured using a white light interferometer under conditions of a pixel number of 640×480, a power spectrum density at a spatial frequency of $1.0 \times 10^{-2}$ $\mu m^{-1}$ calculated from a result of the measurement is $6.0 \times 10^{7}$ $nm^{4}$ or less.

According to Configuration 7 of this invention, through including the defect inspection step of selecting a mask blank substrate having a predetermined surface profile and making defect inspection in a method using two beam interference with regard to the main surface on a side on which the transfer pattern of the mask blank substrate is formed and in the transfer pattern formation region, detection of a false defect may be suppressed when defect inspection of the two beam interference method is made. Therefore, even when defect inspection of the two beam interference method is made, a mask blank substrate that may clarify a fatal defect may be produced.

(Configuration 8)

Configuration 8 of this invention is a method of manufacturing a mask blank substrate according to Configuration 7, wherein the main surface of the mask blank substrate on the side on which the transfer pattern is formed has such a surface profile that, when a measurement region of 693 µm×520 µm of the main surface in the transfer pattern formation region is measured using the white light interferometer under conditions of a pixel number of 640×480, a power spectrum density at a spatial frequency of $5.0 \times 10^{-2}$ $\mu m^{-1}$ calculated from a result of the measurement is $3.0 \times 10^{5}$ $nm^{4}$ or less.

According to Configuration 8 of this invention, detection of a false defect may be further suppressed when defect inspection of a mask blank substrate is made using a defect inspection apparatus of the two beam interference method, which enables production of a mask blank substrate that may further clarify a fatal defect.

(Configuration 9)

Configuration 9 of this invention is a method of manufacturing a mask blank substrate according to Configuration 7 or 8, wherein the main surface of the mask blank substrate on the side on which the transfer pattern is formed has such a surface profile that, when a measurement region of 140 µm×105 µm of the main surface in the transfer pattern formation region is measured using the white light interferometer under conditions of a pixel number of 640×480, a power spectrum density at a spatial frequency of $2.0 \times 10^{-1}$ $\mu m^{-1}$ calculated from a result of the measurement is $8.0 \times 10^{2}$ $nm^{4}$ or less.

According to Configuration 9 of this invention, detection of a false defect may be further suppressed when defect inspection of a mask blank substrate is made using the defect inspection apparatus of the two beam interference method, which enables production of a mask blank substrate that may further clarify a fatal defect.

(Configuration 10)

Configuration 10 of this invention is a method of manufacturing a mask blank substrate according to any one of Configurations 7 to 9, further comprising, before the defect inspection step, a polishing step of polishing the main surface of the mask blank substrate on the side on which the transfer pattern is formed through relatively moving the mask blank substrate on a polishing pad of a polishing surface plate while supplying a polishing liquid thereto.

According to Configuration 10 of this invention, through including the predetermined polishing step, a predetermined surface profile may be obtained on the mask blank substrate, and thus, detection of a false defect may be suppressed with reliability when defect inspection of a mask blank substrate is made using the defect inspection apparatus of the two beam interference method, which enables production of a mask blank substrate that may clarify a fatal defect with reliability.

(Configuration 11)

Configuration 11 of this invention is a method of manufacturing a mask blank substrate according to Configuration 10, wherein the polishing liquid contains colloidal silica having a mean particle size D50 of 100 nm or less.

According to Configuration 11 of this invention, in the predetermined polishing step, a predetermined surface profile may be obtained with more reliability on the mask blank substrate by using a predetermined polishing liquid. Therefore, detection of a false defect may be suppressed with more reliability when defect inspection of a mask blank substrate is made using the defect inspection apparatus of the two beam interference method, which enables production of a mask blank substrate that may clarify a fatal defect with more reliability.

(Configuration 12)

Configuration 12 of this invention is a method of manufacturing a mask blank, comprising a step of forming, on the main surface of the mask blank substrate, a thin film for forming a transfer pattern, on the side on which the transfer pattern is formed, the mask blank substrate being produced by the method of manufacturing a mask blank substrate of any one of Configurations 7 to 11.

According to Configuration 12 of this invention, a mask blank substrate produced by the above-mentioned manufacturing method may have a main surface having a predetermined surface profile. Therefore, detection of a false defect may be suppressed when defect inspection of the thin film for forming the transfer pattern of the mask blank is made using the defect inspection apparatus of the two beam interference method, which enables production of a mask blank that may clarify a fatal defect existing on the mask blank.

(Configuration 13)

Configuration 13 of this invention is a method of manufacturing a transfer mask, comprising a step of forming the transfer pattern in the thin film of the mask blank produced by the method of manufacturing a mask blank of Configuration 12.

According to Configuration 13 of this invention, the transfer mask is produced using a mask blank substrate with a main surface having a predetermined surface profile, and thus, detection of a false defect may be suppressed when defect inspection of the transfer mask is made using the defect inspection apparatus of the two beam interference method, which enables production of a transfer mask that may clarify a fatal defect existing on the transfer mask.

Effect of the Invention

According to this invention, there is provided the mask blank substrate and the manufacturing method thereof that may, even when defect inspection of main surfaces of substrates is made using the defect inspection apparatus of the two beam interference method, suppress remarkable difference from being made in the number of detected false defects among the substrates. Further, according to this invention, there is provided the mask blank, the transfer mask, and the manufacturing methods thereof that may, even when defect inspection of main surfaces of mask blanks or transfer masks is made using the defect inspection apparatus of the two beam interference method, suppress remarkable difference from being made in the number of detected false defects among the mask blanks or the transfer masks. The transfer mask according to this invention may be used as a transmission type transfer mask.

MODE FOR EMBODYING THE INVENTION

[Mask Blank Substrate 10]

First, a mask blank substrate 10 according to an embodiment of this invention is described below.

Figure 1A:
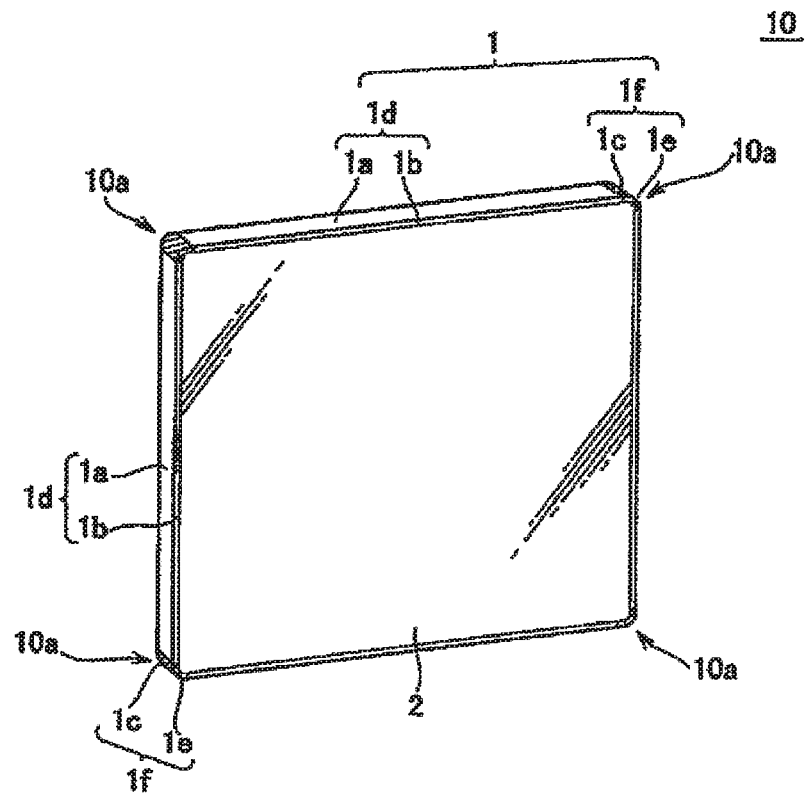
FIG. 1A is a perspective view for illustrating a mask blank substrate according to an embodiment of this invention.
Figure 1B:
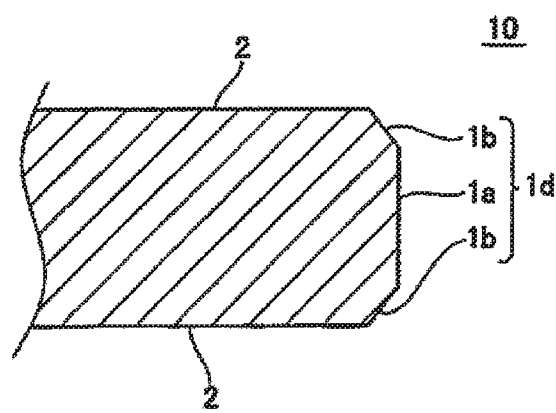
FIG. 1B is a schematic sectional view for illustrating the mask blank substrate according to the embodiment of this invention.

FIG. 1A is a perspective view for illustrating the mask blank substrate 10 of this embodiment. FIG. 1B is a schematic sectional view for illustrating the mask blank substrate 10 of this embodiment.

The mask blank substrate 10 (or simply referred to as "substrate 10") is a plate-like body in a rectangular shape, and has two opposed main surfaces 2 and end surfaces 1. The two opposed main surfaces 2 are an upper surface and a lower surface of the plate-like body, and are formed so as to be opposed to each other. Further, at least one of the two opposed main surfaces 2 is a main surface on which a transfer pattern is to be formed.

The end surface 1 is a side surface of the plate-like body, and is adjacent to edges of the opposed main surfaces 2. The end surface 1 has a planar end surface portion 1d and a curved end surface portion 1f. The planar end surface portion 1d is a surface that connects a side of one opposed main surface 2 and a side of another opposed main surface 2, and includes a side surface portion 1a and chamfered portions 1b. The side surface portion 1a is a portion (T plane) approximately perpendicular to the opposed main surfaces 2 of the planar end surface portion 1d. The chamfered portion 1b is a chamfered portion (C plane) between the side surface portion 1a and the opposed main surface 2, and is formed between the side surface portion 1a and the opposed main surface 2.

The curved end surface portion 1f is a portion (R portion) adjacent to a vicinity of a corner portion 10a of the substrate 10 when the substrate 10 is seen in plan view, and includes a side surface portion 1c and chamfered portions 1e. Here, the phrase "the substrate 10 is seen in plan view" means that the substrate 10 is seen from, for example, a direction perpendicular to the opposed main surfaces 2. Further, the corner portion 10a of the substrate 10 is, for example, a vicinity of an intersection of two sides at edges of the opposed main surfaces 2. An intersection of two sides may be an intersection of extensions of the two sides. In this example, the curved end surface portion 1f is formed so as to be curved by rounding the corner portion 10a of the substrate 10.

This invention has a feature in that, in order to attain the objects described above, at least a main surface on a side on which a transfer pattern is formed, i.e., in a transmission type mask blank 50, as described below, a main surface on a side on which a thin film for forming a pattern (light-shielding film 51 or the like) has a specific power spectrum density (PSD) in a specific spatial frequency region.

The power spectrum density (PSD) corresponding to a parameter indicating a surface profile of the main surface of the mask blank substrate 10 of this invention and a surface roughness (Rms) and a flatness corresponding to other parameters that the mask blank substrate 10 of this invention preferably satisfies are described below.

<Power Spectrum Density>

Through Fourier transform of unevenness of the substrate main surface obtained through measuring the surface of the mask blank substrate 10 using, for example, a white light interferometer or an atomic force microscope, the unevenness may be represented by amplitude intensity at a predetermined spatial frequency. This is measured data of the unevenness (i.e., minute profile of the substrate main surface) represented as a sum of waves at predetermined spatial frequencies, that is, the surface profile of the substrate divided into waves at the predetermined spatial frequencies.

Such power spectrum analysis may convert minute surface profile of the substrate into a numerical form. When data (value) of height in a specific x coordinate and a specific y coordinate on the surface profile is represented by Z (x, y), Fourier transform F (u,v) thereof is given by Expression (2) below:

[Math. 1]

$$F(u, v) = \frac{1}{N_x N_y} \sum_{x=0}^{N_x-1} \sum_{y=0}^{N_y-1} Z(x, y) \exp\left[-i2\pi\left(\frac{ux}{N_x} + \frac{vy}{N_y}\right)\right] \quad (2)$$

Here, Nx and Ny are the numbers of data in an x direction and a y direction, respectively, and u=0, 1, 2 ... Nx−1 and v=0, 1, 2 ... Ny−1 are established. A spatial frequency f at this time is given by Expression (3) below.

[Math. 2]

$$f = \left\{ \left[\frac{u}{(N_x - 1)d_x}\right]^2 + \left[\frac{v}{(N_y - 1)d_y}\right]^2 \right\}^{1/2} \quad (3)$$

(In Expression (3), $d_x$ is a minimum resolution in the x direction and $d_y$ is a minimum resolution in the y direction.)

The power spectrum density P(u,v) at this time is given by Expression (4) below:

[Math. 3]

$$P(u,v) = |F(u,v)|^2 \quad (4)$$

This power spectrum analysis is excellent in that change in surface state of the substrate may be grasped not only as simple change in height but also as change thereof in the spatial frequency, and is a method of analyzing how a microscopic reaction on an atomic level and the like affects the main surface of the substrate.

In order to attain the objects described above, the mask blank substrate 10 according to this invention has a power spectrum density (PSD) of $6.0 \times 10^7$ $nm^4$ or less at a spatial frequency of $1.0 \times 10^{-2}$ $\mu m^{-1}$ obtained when a region of 2.8 mm×2.1 mm of the main surface on the side on which the transfer pattern is formed is measured by a white light interferometer with a pixel number of 640×480.

As an apparatus for measuring a surface state of a substrate, a white light interferometer is known. A white light interferometer is an apparatus using a method in which, for example, white light that is less coherent is used as a light source, an equal optical path interferometer such as of a Mirau type or a Michelson type is used, and an equal optical path position (position at which the interference intensity is at the maximum) of each of CCD pixels corresponding to a measured surface is found through vertical scanning of an interferometer objective lens. Examples of the white light interferometer include a noncontact surface profile measuring machine "NewView 7000 Series" produced by Zygo Corporation.

The region of 2.8 mm×2.1 mm is herein a region at the center of the mask blank substrate 10. For example, when the main surface of the mask blank substrate 10 is in the shape of a rectangle, the center described above is an intersection of diagonal lines of the rectangle. In other words, the intersection and the center of the region (the center of the region is similar to the center of the substrate) spatially match to each other. The same applies to a case in which the surface profile of a thin film such as a thin film for forming a patter (for example, light-shielding film 51).

Further, when the spatial frequency of $1.0 \times 10^{-2}$ $\mu m^{-1}$ is observed, observation of the region of 2.8 mm×2.1 mm using a white light interferometer with a pixel number of 640×480 increases the reliability of the data. In this invention, the PSD data in the region at the spatial frequency described above is assumed to be obtained through observation under measurement conditions (measurement field of view and the like) that are assumed to be of high reliability.

It is preferred that, in addition to the observation at the spatial frequency of $1.0 \times 10^{-2}$ $\mu m^{-1}$, the mask blank substrate 10 according to this invention have such a surface profile that the main surface on the side on which the transfer patter is formed has a power spectrum density of $3.0 \times 10^5$ $nm^4$ or less at a spatial frequency of $5.0 \times 10-2$ $\mu m^{-1}$ calculated from the result of measurement in which a measurement region of 693 µm×520 µm of the main surface in the transfer pattern formation region is measured using a white light interferometer under conditions of a pixel number of 640×480. As a result, the reliability of the data increases, and thus, detection of a false defect may be further suppressed when defect inspection of the mask blank substrate 10 is made using a defect inspection apparatus of a two beam interference method, which may further clarify a fatal defect.

It is preferred that, in addition to the observation at the spatial frequency of $1.0 \times 10^{-2}$ $\mu m^{-1}$ and $5.0 \times 10^{-2}$ $\mu m^{-1}$, the mask blank substrate 10 according to this invention have such a surface profile that the main surface on the side on which the transfer pattern is formed has a power spectrum density of $8.0 \times 10^2$ $nm^4$ or less at a spatial frequency of $2.0 \times 10^{-1}$ $\mu m^{-1}$ calculated from the result of measurement in which a measurement region of 140 µm×105 µm of the main surface in the transfer pattern formation region is measured using a white light interferometer under conditions of a pixel number of 640×480. As a result, the reliability of the data increases even further, and thus, detection of a false defect may be suppressed even further when defect inspection of the mask blank substrate 10 is made using a defect inspection apparatus of a two beam interference method, which may clarify a fatal defect even further.

It is preferred that, in the mask blank substrate 10 according to this invention, the main surface on a side different from the side on which the transfer pattern is formed also be within a range of a predetermined power spectrum density at a predetermined spatial frequency as in the main surface in the transfer pattern formation region. For example, it is preferred that the mask blank substrate 10 according to this invention have such a surface profile that the main surface on the side different from the side on which the transfer pattern is formed has a power spectrum density of $6.0 \times 10^7$ $nm^4$ or less at a spatial frequency of $1.0 \times 10^{-2}$ $\mu m^{-1}$ calculated from the result of measurement in which a measurement region of 2.8 mm×2.1 mm of the main surface in a region having the same size as the transfer pattern formation region is measured using a white light interferometer under conditions of a pixel number of 640×480. As a result, even on the main surface on the side different from the side on which the transfer pattern is formed, detection of a false defect may be suppressed when defect inspection of the mask blank substrate 10 is made using a defect inspection apparatus of a two beam interference method, which may clarify a fatal defect.

In order to produce a transmission type transfer mask 60, it is necessary to make defect inspection of main surfaces of the mask blank substrate 10, a mask blank 50, and the transfer mask 60. As a defect inspection method, there are a defect inspection method as a two beam interference method and a defect inspection method as a spatial filter method. The mask blank substrate 10, the mask blank 50, and the transfer mask 60 according to this invention may, when defect inspection of the main surfaces thereof are made using the two beam interference method, suppress remarkable difference from being made in the number of detected false defects among the mask blank substrates 10, among the mask blanks 50, and among the transfer masks 60. Therefore, in the mask blank substrate 10, the mask blank 50, and the transfer mask 60 according to this invention, while the number of detected defects including false defects may be reduced, a fatal defect that is required to be detected without fail may be detected with reliability. This may make a fatal defect clarification, and, when a fatal defect is detected, various measures may be taken including removing the fatal defect, and designing a mask so that a thin film pattern (transfer pattern such as a light-shielding film pattern 51a) lies on the fatal defect in the transfer mask 60 described below.

<Surface Roughness (Rms)>

Root means square (Rms), which is a typical index of the surface roughness of the mask blank substrate 10, is a root mean square roughness, and is a square root of a mean value of squares of deviations from an average line to a measurement curve. Specifically, Rms is expressed by Expression (1) below.

[Math. 4]

$$\mathrm{Rms} = \sqrt{\frac{1}{l}\int_0^l Z^2(x)\,dx} \quad (1)$$

(In Expression (1), l is a reference length and Z is a height from the average line to the measurement curve.)

Rms may be obtained through measurement of a region of 1 µm×1 µm of the main surface of the mask blank substrate 10 using an atomic force microscope.

Further, the root mean square roughness (Rms) described above is preferably less than 0.13 nm, more preferably 0.12 nm or less, and further preferably 0.10 nm or less. The root mean square roughness as used here is a value in a case of calculation from the result of measurement of a region inside a square of 1 µm×1 µm of the substrate main surface using an atomic force microscope.

<Flatness>

Further, it is preferred that, in the mask blank substrate 10 according to this embodiment, the main surface on the side on which the transfer patter is formed be surface treated so as to be highly flat from the viewpoint of obtaining at least pattern transfer accuracy and positional accuracy. In the case of the mask blank substrate 10 used for a transmission type mask blank for light exposure of ArF excimer laser, in a region inside of a square of 132 mm×132 mm or in a region inside of a square of 142 mm×142 mm of the main surface of the substrate 10 on the side on which the transfer pattern is formed, the flatness is preferably 0.3 µm or less, and particularly preferably 0.2 µm or less. Further, the main surface on the side opposite to the side on which the transfer pattern is formed is required to have a similar flatness.

[Method of Manufacturing Mask Blank Substrates 10]

The mask blank substrate 10 according to this invention described above may be produced as follows.

A method of manufacturing the mask blank substrate 10 according to this invention is a method of manufacturing the mask blank substrate 10 being a substrate having two main surfaces, and includes a defect inspection step of making defect inspection using the two beam interference method with regard to the main surface of the mask blank substrate 10 on the side on which the transfer pattern is formed and in the transfer pattern formation region. Further, the main surface of the mask blank substrate 10 on the side on which the transfer pattern is formed has a surface profile achieving a power spectrum density that is equal to or smaller than a predetermined value at a predetermined spatial frequency calculated from the result of measurement that is performed under conditions in which the predetermined measurement region of the main surface in the transfer pattern formation region is measured using a white light interferometer with a predetermined pixel number. The method of manufacturing the mask blank substrate 10 according to this invention includes the defect inspection step of making defect inspection using the two beam interference method, and thus, detection of a false defect in defect inspection using the two beam interference method may be suppressed, which enables production of the mask blank substrate 10 that may clarify a fatal defect.

More specific description is made of the method of manufacturing the mask blank substrate 10 according to this invention.

As a material of the glass substrate, for example, a glass material such as synthetic quartz glass, soda lime glass, aluminosilicate glass, low thermal expansion glass (for example, $SiO_2$—$TiO_2$-based glass), or crystallized glass in which β-quartz solid solution is precipitated may be used. As the material of the glass substrate, it is preferred to use synthetic quartz glass.

The mask blank substrate 10 according to this invention may be produced through performing surface treatment on the main surface on the side on which the transfer pattern is formed such that the main surface has a predetermined surface profile, that is, has a surface profile achieving a power spectrum density (PSD) of $6.0 \times 10^7$ $nm^4$ or less at a spatial frequency of $1.0 \times 10^{-2}$ $\mu m^{-1}$ calculated from the result of measurement that is performed under conditions in which a measurement region of 2.8 mm×2.1 mm is measured using a white light interferometer with a pixel number of 640×480. Methods of the surface treatment of the mask blank substrate 10 are known, and the method adopted in this invention is not specifically limited.

Exemplary methods of the surface treatment of the mask blank substrate 10 include magnetorheological finishing (MRF), chemical mechanical polishing (CMP), gas cluster ion beam etching (GCIB), and dry chemical planarization (DCP) using local plasma etching. MRF is a local treatment method in which abrasive grains contained in magnetic fluid is brought into contact with a workpiece (mask blank substrate 10) at high speed with a residence time of the contact portion being controlled, thereby performing local polishing. CMP is a local treatment method in which a small-diameter polishing pad and a polishing agent (containing abrasive grains of colloidal silica or the like) are used with a residence time of the contact portion between the small-diameter polishing pad and the workpiece (mask blank substrate 10) being controlled, thereby mainly polishing protrusion portions on the surface of the workpiece. GCIB is a local treatment method in which a reactive material in gaseous form at normal temperature and pressure (source gas) is adiabatically expanded in a vacuum device and ejected to generate gas cluster, the gas cluster ions generated through ionization by electron irradiation are accelerated in a high electric field into a gas cluster ion beam, and the gas cluster ion beam is radiated to the workpiece to be etched. DCP is a local treatment method in which plasma etching is locally performed with the plasma etching amount being controlled depending on the extent of the projection, thereby locally performing dry etching.

As a surface treatment method of the mask blank substrate 10, for example, the following method may be used.

In the method of manufacturing the mask blank substrate 10 according to this invention, it is preferred to include, before the defect inspection step, a polishing step of polishing the main surface of the mask blank substrate 10 on the side on which the transfer pattern is formed through relatively moving the mask blank substrate 10 on a polishing pad 17 of a polishing surface plate while supplying a polishing liquid thereto, as a surface treatment method. The method of manufacturing the mask blank substrate 10 according to this invention includes the predetermined polishing step. Therefore, the predetermined surface profile of the mask blank substrate 10 may be obtained, and thus, detection of a false defect may be suppressed with reliability when defect inspection of the mask blank substrate 10 is made using a defect inspection apparatus of the two beam interference method, which enables production of the mask blank substrate 10 that may clarify a fatal defect with reliability.

A preferred method as a surface treatment method of the mask blank substrate 10 (referred to as "this surface treatment method") is as follows. First, the mask blank substrate 10 is set on the surface plate including the polishing pad 17 on a rotating surface thereof. Then, the mask blank substrate 10 is relatively moved with respect to a polishing surface of the polishing pad 17 while the polishing liquid containing abrasive grains of silica or colloidal silica is supplied between the polishing pad 17 and the substrate, thereby polishing the main surface of the substrate. At that time, the polishing pad 17 includes at least a base material 17A and a nap layer 17B formed on the base material 17A and formed of a foamed resin having pores in a surface thereof. It is preferred that the polishing pad 17 have a compression deformation amount of 330 µm or less and that the resin forming the nap layer 17B have a 100% modulus of 3 MPa or more and 14 MPa or less.

With such a surface treatment method of the mask blank substrate 10, an undulation of the substrate main surface after the polishing may be suppressed, and, as a result, a substrate having a high flatness may be produced. Further, such a surface treatment method may set the main surface of the mask blank substrate 10 to be within the range of a predetermined power spectrum density at the predetermined spatial frequency. Therefore, detection of a false defect may be suppressed when defect inspection of the mask blank substrate 10 is made using a defect inspection apparatus of the two beam interference method, which may clarify a fatal defect.

Figure 7:
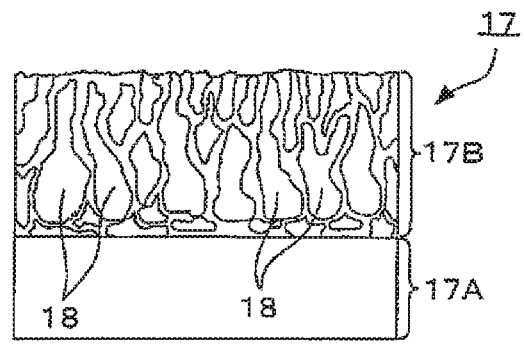
FIG. 7 is a schematic view for illustrating sectional structure of a polishing pad.

FIG. 7 is a schematic view for illustrating the sectional structure of the polishing pad 17 used in this surface treatment method.

As illustrated in FIG. 7, the polishing pad 17 used in the polishing includes the base material 17A formed of a nonwoven fabric, a resin film of a PET resin, or the like, and the nap layer 17B formed on the base material 17A and formed of a foamed resin having pores in the surface thereof.

Although not illustrated, a buffer layer may be included between the base material 17A and the nap layer 17B. The buffer layer is arranged for the purpose of adjusting a compression deformation amount of the entire polishing pad 17, and is preferably a foamed resin.

Hollow portions called pores 18 being traces of foam exist in the foamed resin layer. In FIG. 7, for the sake of convenience of illustration, the sectional internal structure of the polishing pad 17 (in particular, the nap layer 17B) is drawn merely for illustration purposes, and actual internal structure is not necessarily drawn with accuracy.

In this polishing pad 17, the foamed resin means, for example, one in which gas is finely dispersed in a synthetic resin into a foamed or porous shape containing an infinite number of fine forms therein, and may also be defined as a nonuniform disperse system of gas and the synthetic resin being a solid. In this polishing pad 17, as the foamed resin (nap layer 17B), urethane is widely used. When the foamed resin (nap layer 17B) is a polyurethane resin, as a material resin forming the polyurethane resin, a resin that is polycarbonate-based, polyester-based, polyether-based, or the like or a resin formed by blending thereof may be used.

Exemplary polishing pads 17 including the base material 17A and the nap layer 17B include a suede type polishing pad and a foamed urethane type polishing pad. A suede type polishing pad 17 is formed through coating the base material 17A with polyurethane (lamination), growing a foamed layer in the polyurethane, and removing a surface portion to form an opening in the foamed layer. Further, a foamed urethane type polishing pad 17 is formed through slicing a block of foamed urethane. Through joining the slice with the base material 17A, the polishing pad 17 including the base material 17A and the foamed resin layer (nap layer 17B) may be formed. When there are a plurality of foamed resin layers, the foamed resin layers are joined together. It is preferred that the nap layer 17B have a thickness of, for example, from about 300 µm to about 1,000 µm. Further, it is preferred that the pores in the nap layer 17B have an opening diameter of, for example, from about 40 µm to about 100 µm.

This polishing pad 17 has a structural feature in that a combination of the compression deformation amount of the polishing pad 17 and the modulus of the resin forming the nap layer 17B is appropriately selected. Specifically, in the polishing pad 17, it is preferred that the polishing pad 17 have a compression deformation amount of 330 µm or less, and, at the same time, the resin forming the nap layer 17B have a 100% modulus of 3 MPa or more and 14 MPa or less.

Figure 9:
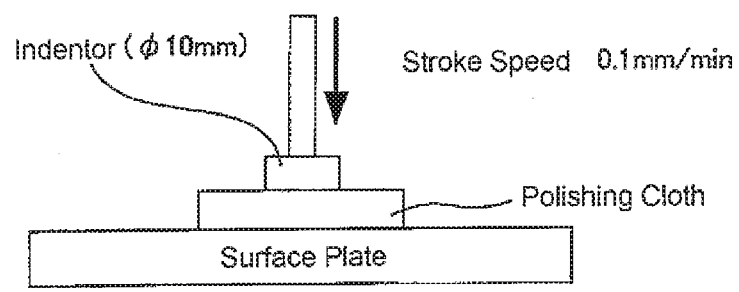
FIG. 9 is a structural view of a compression tester used in measuring a compression deformation amount of the polishing pad.
Figure 10:
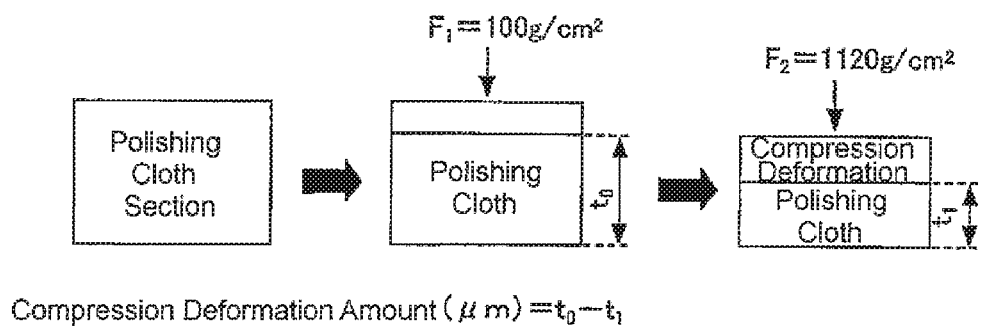
FIG. 10 is a schematic view for illustrating a method of measuring the compression deformation amount of the polishing pad.

According to this invention, the compression deformation amount of the polishing pad 17 is, as illustrated in FIG. 10, represented by compression deformation amount $(\mu m)=t_0-t_1$, where a thickness of the polishing pad 17 when a load $F_1=100$ g/cm² is applied in a thickness direction of the polishing pad 17 (polishing cloth) is $t_0$, and a thickness of the polishing pad 17 when, thereafter, a load $F_2=1,120$ g/cm² is applied is $t_1$. Further, compressibility (%) is represented by $[(t_0-t_1)/t_0] \times 100$. The compression deformation amount is measured using, as, for example, as illustrated in FIG. 9, a compression tester, and the polishing pad 17 is mounted on the surface plate and the polishing pad 17 is pressed from above with an indenter (ϕ10 mm) with a stroke speed of 0.1 mm/min.

Further, according to this invention, a resin modulus is an indicator designating hardness of the resin itself. A resin modulus is expressed as force applied when a non-foamed resin film is extended twice as long (tensile stress). As the resin becomes harder, stronger force is necessary to extend the resin, and thus, the value becomes larger. As the resin becomes softer, the value becomes smaller. A method of measuring the resin modulus is described below.

(1) A resin solution is spread thin and is dried with hot air to form a dry film having a thickness of about 50 µm.

(2) The film is matured for a while after being formed.

(3) A strip-like sample to be measured having a length of 20 mm, a width of 5 mm, and a thickness of 0.05 mm is pulled at a pulling speed of 300 mm/min.

(4) A tension when the sample is extended by 100% (extended twice as long) is divided by an initial cross section of the sample to determine the 100% modulus (in MPa).

(5) A mean value of the number of the samples n=7 is determined.

The resin modulus depends not on the base of the resin (the kind of the resin such as polycarbonate-based, polyester-based, or polyether-based) but basically on the content of a hard segment. Specifically, polyurethane has a soft segment and a hard segment, and has a microphase separation structure, and thus, the ratio (amount) of the hard segment determines the hardness of the resin. The hard segment is isocyanate and a low-molecular diol, at which the resin (high molecule) coagulates strongly and at which movement of the high molecule=soft segment is fixed. The soft segment is a high molecule polyol at which the resin (high molecule) coagulates weakly. The soft segment may be adjusted by a blend ratio of the base of the resin (the kind of the resin such as polycarbonate-based, polyester-based, or polyether-based) and the resin.

It is preferred that the polishing pad 17 applied in the polishing step have a compression deformation amount of 330 µm or less. Further, it is preferred that the 100% modulus of the resin forming the nap layer 17B be optimally 3 MPa or more and 14 MPa or less. If the polishing pad 17 has a compression deformation amount of more than 330 µm, for example, an undulation PV value is 10 nm or more, and an undulation cannot be suppressed. On the other hand, when the resin forming the nap layer has a 100% modulus of less than 3 MPa, it is difficult to suppress an undulation. Further, when the 100% modulus exceeds 14 MPa, although an undulation may be suppressed, there is a problem in that a large number of flaw defects are caused on the substrate main surface after the polishing.

In this surface treatment method, it is preferred that the polishing pad 17 have a compression deformation amount of, in particular, 60 µm or more and 300 µm or less, and more preferably, 75 µm or more and 260 µm or less. Further, it is particularly preferred that the resin forming the nap layer have a 100% modulus of 6 MPa or more and 12 MPa or less.

Through polishing the substrate main surface using the polishing pad 17 having the characteristics described above, an undulation of the substrate main surface after the polishing may be suppressed. As a result, with the transfer mask described above, a substrate with a high degree of flatness that may realize a flatness of, for example, 30 nm or less may be produced. Further, such a surface treatment method may set the main surface of the mask blank substrate 10 to be within the range of the predetermined power spectrum density at the predetermined spatial frequency. Therefore, detection of a false defect may be suppressed when defect inspection of the mask blank substrate 10 is made using a defect inspection apparatus of the two beam interference method, which may clarify a fatal defect.

In a method of manufacturing the mask blank substrate 10 using this surface treatment method, a polishing step to which the polishing pad 17 having the characteristics described above is applied is performed. Specifically, in the polishing step, the substrate is set on the surface plate including the polishing pad 17 on the rotating surface thereof, and the substrate is relatively moved with respect to the polishing surface of the polishing pad 17 while the polishing liquid containing abrasive grains of silica or colloidal silica is supplied between the polishing pad 17 and the substrate, thereby polishing the main surface of the substrate.

Figure 8:
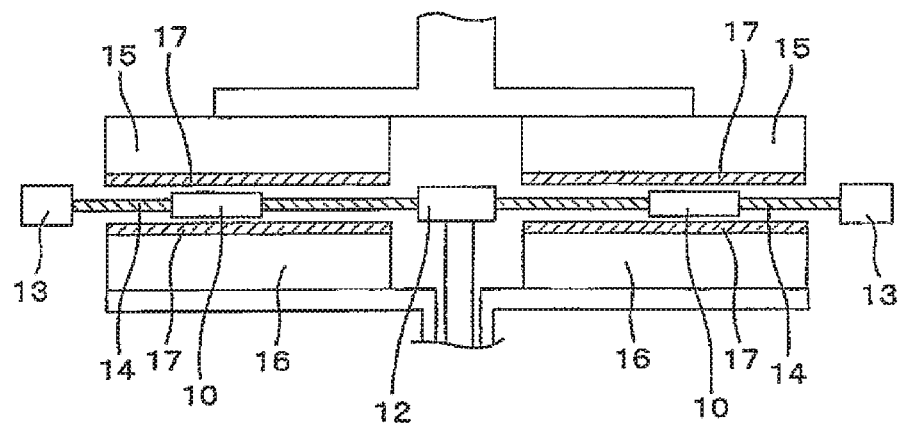
FIG. 8 is a structural view of a double side polisher.

Such a polishing step may be performed using, for example, a planetary gear type double side polisher as illustrated in FIG. 8. The double side polisher illustrated in FIG. 8 includes a sun gear 12, internal gears 13 concentrically arranged outside thereof, a carrier 14 engaged with the sun gear 12 and the internal gears 13 and revolves and rotates in accordance with rotation of the sun gear 12 and the internal gears 13, an upper surface plate 15 and a lower surface plate 16 each having the polishing pad 17 bonded thereto that may sandwich a workpiece to be polished (mask blank substrate 10) held by the carrier 14, and a polishing liquid supply unit (not shown) configured to supply the polishing liquid between the upper surface plate 15 and the lower surface plate 16.

In the polishing using such a double side polisher, the workpiece to be polished, i.e., the substrate 10 (glass substrate) held by the carrier 14 is sandwiched between the upper surface plate 15 and the lower surface plate 16. While the polishing liquid is supplied between the polishing pad 17 on the upper surface plate 15 and the polishing pad 17 on the lower surface plate 16 and the substrate 10, the carrier 14 revolves and rotates in accordance with rotation of the sun gear 12 and the internal gears 13, thereby polishing upper and lower main surfaces of the substrate 10. Through using such a double side polisher, both of the main surfaces of the substrate 10 may be simultaneously polished. The main surfaces of the substrate 10 may also be polished one by one using a single side polisher.

In this surface treatment method, it is desired to perform a rough polishing step, a precision polishing step, and an ultra-precision polishing step using, for example, the double side polisher described above. Further, according to this invention, it is preferred to apply, in the ultra-precision polishing step, the polishing pad 17 having the characteristics described above.

The kind and the particle size of the polishing agent used may be appropriately selected depending on the substrate material and target flatness. Exemplary polishing agents include cerium oxide, zirconium oxide, silica, and colloidal silica. The particle size of the polishing agent ranges from several tens of nanometers to several micrometers. The method of manufacturing the mask blank substrate 10 according to this invention is optimum when the substrate is polished with a polishing liquid containing silica or colloidal silica.

From the viewpoint of reducing as much as possible recess defects such as pits on the main surface of the mask blank substrate 10, it is preferred that the abrasive grains used in this surface treatment method or the like be colloidal silica. Further, it is preferred that the polishing liquid containing colloidal silica contain water, and further, contain a predetermined additive (for example, an alkaline compound). The additive has, in addition to the function of forming a coating on a particle surface, the function of protecting a surface to be polished to suppress the surface to be polished from being damaged by the abrasive grains.

The additive contained in the polishing liquid is preferably at least one kind selected from hydroxyethylcellulose, hydroxypropylcellulose, polyvinyl alcohol, polyvinylpyrrolidone, and pullulan. Two or more kinds thereof may also be used as a mixture. The additive contained in the polishing liquid is most preferably hydroxyethylcellulose in consideration of washability. In addition, examples of the alkali compound contained as the additive in the polishing liquid include tetramethylammonium hydroxide, tetraethylammonium hydroxide, and tetrabutylammonium hydroxide. The alkali compound contained as the additive in the polishing liquid is preferably ammonia.

The rough polishing step is performed for the purpose of removing a flaw on the substrate main surface formed in a grinding step to maintain flatness obtained in the grinding step, and is a step of performing polishing using abrasive grains that have a relatively large mean particle size of from about 1 µm to about 3 µm. A material of the abrasive grains is appropriately selected depending on the material of the substrate. It is preferred that the polishing pad 17 used in the rough polishing step be a hard polisher from the viewpoint of maintaining the flatness.

The precision polishing step is performed for the purpose of mirror polishing the substrate with no surface defect such as a flaw, and is a step of performing polishing using abrasive grains that have a relatively small mean particle size of about 1 µm or less (for example, from 10 nm to 1 µm). Similarly to the above, a material of the abrasive grains is appropriately selected depending on the material of the substrate. From the viewpoint of being able to obtain a smooth substrate main surface with a small mean particle size, cerium oxide is preferred. It is preferred that the polishing pad 17 used in the precision polishing step be a soft or ultrasoft polisher from the viewpoint of mirror polishing.

The ultra-precision polishing step is performed for the purpose of further mirror polishing the substrate (improving the surface roughness), and is a step of performing polishing using abrasive grains that have a very small mean particle size of about 500 nm or less (for example, from 10 nm to 500 nm). Similarly to the above, a material of the abrasive grains is appropriately selected depending on the material of the substrate. From the viewpoint of being able to obtain a smooth substrate main surface with a small mean particle size, silica or colloidal silica is preferred, and colloidal silica is particularly preferred. It is preferred that the polishing pad 17 used in the ultra-precision polishing step be a soft or ultrasoft polisher from the viewpoint of further mirror polishing. In this invention, from the viewpoint of reducing an undulation and obtaining the predetermined spatial frequency, the polishing pad 17 having the compression deformation amount and the 100% modulus described above is used.

According to this invention, it is preferred that the polishing liquid used in the predetermined polishing step contain colloidal silica having a mean particle size D50 (particle size at 50% of an integrated value of all the particles) of 100 nm or less. Through using the predetermined polishing liquid, the predetermined surface profile may be obtained on the mask blank substrate 10 with more reliability. Thus, detection of a false defect may be suppressed with more reliability when defect inspection of the mask blank substrate 10 is made using a defect inspection apparatus of the two beam interference method, which enables production of the mask blank substrate 10 that may clarify a fatal defect with more reliability.

In this surface treatment method, it is preferred to perform, after the polishing step described above, a surface profile information measuring step of measuring surface profile information (for example, uneven shape) of the glass substrate main surface, a local treatment step of applying local treatment with treatment conditions being set with regard to the respective places on the main surface so as to attain a desired flatness based on the result of measurement obtained in the surface profile information measuring step, and a finishing polishing step of, after the local treatment step, performing finishing polishing so as to attain a desired smoothness. The local treatment methods described above are applicable in the local treatment step.

The finishing polishing step is performed for the purpose of, when surface roughness or a layer deteriorated by the treatment is caused on the glass substrate main surface in the local treatment step, removing the surface roughness or the deteriorated layer. When surface roughness or a layer deteriorated by the treatment, which is required to be removed, is not caused on the glass substrate main surface, the finishing polishing is not particularly necessary.

As a method of the finishing polishing, a polishing method that maintains the flatness obtained in the local treatment step and still improves the surface roughness is preferred. Exemplary methods include a precision polishing method in which polishing is performed with a polishing liquid under a state in which the glass substrate main surface is in contact with a surface of a polishing tool such as the polishing pad 17, a noncontact polishing method in which the glass substrate main surface and a polishing tool surface are not brought into direct contact with each other and polishing is performed by the action of a treatment fluid therebetween (for example, float polishing method or elastic emission machining (EEM) method). Further, catalyst-referred etching (CARE) may also be used.

[Method of Manufacturing Mask Blank 50]

This invention is the mask blank 50 having a feature in that the main surface of the mask blank substrate 10 on the side on which the transfer pattern is formed has formed thereon a thin film for forming the transfer pattern. With the mask blank 50 of this invention, through using the mask blank substrate 10 having the main surface that has the predetermined surface profile, detection of a false defect may be suppressed when defect inspection of the thin film for forming the transfer pattern of the mask blank 50 is made using a defect inspection apparatus of the two beam interference method, which may clarify a fatal defect existing on the mask blank 50.

Figure 2:
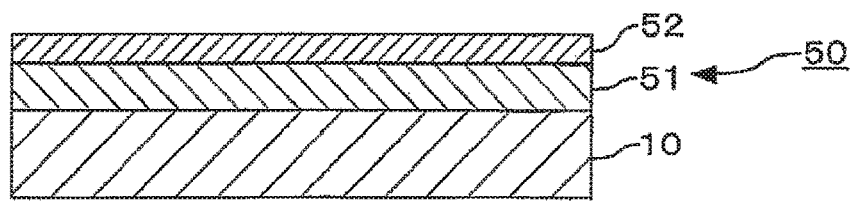
FIG. 2 is a schematic sectional view for illustrating exemplary structure of a mask blank according to the embodiment of this invention.

FIG. 2 is a schematic sectional view for illustrating exemplary structure of the mask blank 50 (transmission type mask blank 50) according to this invention. The mask blank 50 according to this invention may be produced as follows. The mask blank 50 according to this invention may be produced through forming the thin film for forming the pattern (light-shielding film 51 or the like) on the main surface of the mask blank substrate 10 produced as described above on the side on which the transfer pattern is formed. In the case of the mask blank 50 illustrated in FIG. 2, an etching mask film 52 is further formed on the surface of the light-shielding film 51.

The mask blank 50 according to this invention may be applied to, for example, the mask blank 50 of (1) to (3) below.

(1) A binary type mask blank 50 including the light-shielding film 51 formed of a material containing a transition metal Such binary type mask blank 50 has a form having the light-shielding film (thin film) 51 on the main surface of the substrate, and the light-shielding film 51 is formed of a material containing a transition metal single substance, such as chromium, tantalum, ruthenium, tungsten, titanium, hafnium, molybdenum, nickel, vanadium, zirconium, niobium, palladium, rhodium, tin, or indium, or a compound thereof. An example thereof is the light-shielding film 51 constituted of a tantalum compound in which one or more kinds of elements selected from elements, such as oxygen, nitrogen, and boron, are added to tantalum.

The binary type mask blank 50 includes one in which the light-shielding film 51 has a two-layer structure of a light-shielding layer and a front surface antireflection layer and one in which the light-shielding film 51 has a three-layer structure of the light-shielding layer and the substrate, and a back surface antireflection layer being further added therebetween.

Further, the light-shielding film 51 may be a composition gradient film in which the composition thereof varies in a continuous or stepwise manner in a film thickness direction.

(2) A phase shift mask blank including a translucent film formed of a material containing a silicon compound or a material containing a compound of a transition metal and silicon (including a transition metal silicide, in particular, molybdenum silicide).

The phase shift mask blank includes a halftone type phase shift mask blank having a translucent film (thin film) on the substrate main surface. Through patterning the translucent film of the halftone type phase shift mask blank and forming a shifter portion, the halftone type phase shift mask is produced. In the phase shift mask, in order to prevent poor patterning of the transferred substrate using the translucent film pattern formed in a transfer region based on light passing through the translucent film, the substrate main surface may have the translucent film and a light-shielding film (light-shielding band) formed thereon in this order. Further, in addition to the halftone type phase shift mask blank, there is a mask blank for a Levenson type phase shift mask or for an enhancer type phase shift mask of a substrate engraved type in which the substrate is engraved by etching or the like to form the shifter portion.

The translucent film of the halftone type phase shift mask blank passes light having an intensity that substantially does not contribute to exposure (for example, 1% to 30% of the exposure wavelength), and causes a predetermined phase difference (for example, 180°). A translucent portion in which the translucent film is patterned and a light transmitting portion that passes light having an intensity substantially contributing to exposure and that does not have the translucent film formed thereon may cause the phase of light passing through the translucent portion to be substantially in an inverted relationship with the phase of light passing through the light transmitting portion. As a result, light beams passing in the vicinity of a boundary portion between the translucent portion and the light transmitting portion may interfere with each other as a diffraction phenomenon to cancel each other out, thereby causing the light intensity on the boundary portion to be almost zero. In this way, the contrast, i.e., the resolution, on the boundary portion between the translucent portion and the light transmitting portion may be improved.

The translucent film is formed of a material containing, for example, a compound of a transition metal and silicon (including a transition metal silicide). The material includes a material containing such a transition metal and silicon, and oxygen and/or nitrogen as main constituent elements thereof. As the transition metal, there may be applied molybdenum, tantalum, tungsten, titanium, hafnium, nickel, vanadium, zirconium, niobium, palladium, ruthenium, rhodium, chromium, and the like. In addition, the translucent film may be formed of a material containing silicon and nitrogen. In this case, it is preferred that the translucent film have structure in which a low transmission layer having a relatively low nitrogen content and a high transmission layer having a relatively high nitrogen content are laminated at least once.

When the translucent film has the light-shielding film formed thereon, the material of the translucent film contains the transition metal and silicon. Thus, it is preferred that a material of the light-shielding film be formed of chromium having etching selectivity (resistant to etching) with respect to the translucent film or a chromium compound in which an element such as oxygen, nitrogen, or carbon is added to chromium.

A Levenson type phase shift mask is produced from a mask blank having structure similar to that of the binary type mask blank 50, and thus, the structure of the thin film for forming the pattern is similar to that of the light-shielding film 51 of the binary type mask blank 50. The translucent film of a mask blank for an enhancer type phase shift mask passes light having an intensity that substantially does not contribute to exposure (for example, 1% to 30% of the exposure wavelength), but is a film that causes only a small phase difference in exposure light passing therethrough (for example, the phase difference is 30° or less, preferably 0°), and is different from the translucent film of the halftone type phase shift mask blank on this point. A material of the translucent film contains elements similar to those of the translucent film of the halftone type phase shift mask blank, but composition ratios and film thicknesses of the respective elements are adjusted so as to attain a predetermined transmittance and a predetermined small phase difference with respect to the exposure light.

(3) A binary type mask blank 50 including the light-shielding film 51 formed of a material containing a compound of a transition metal and silicon (including a transition metal silicide, in particular, molybdenum silicide)

The light-shielding film 51 (thin film) is formed of a material containing a compound of a transition metal and silicon. Alternatively, the light-shielding film 51 (thin film) is formed of a material containing a transition metal and silicon, and oxygen and/or nitrogen as main constituent elements thereof. Alternatively, the light-shielding film 51 is formed of a material containing a transition metal, and oxygen, nitrogen, and/or boron as main constituent elements thereof. As the transition metal, there may be applied molybdenum, tantalum, tungsten, titanium, hafnium, nickel, vanadium, zirconium, niobium, palladium, ruthenium, rhodium, chromium, and the like.

In particular, when the light-shielding film 51 is formed of a compound of molybdenum silicide, the light-shielding film 51 may have a two-layer structure of a light-shielding layer (such as MoSiN) and a front surface antireflection layer (such as MoSiN), or the light-shielding film 51 may have a three-layer structure with a back surface antireflection layer (such as MoSiON) being further added between the light-shielding layer and the substrate.

Further, the light-shielding film 51 may be a composition gradient film in which the composition thereof varies in a continuous or stepwise manner in the film thickness direction.

Further, in order to thin a resist film and to form a fine pattern therein, the etching mask film 52 may be formed on the light-shielding film 51. The etching mask film 52 has etching selectivity (resistant to etching) with respect to etching of the light-shielding film 51 containing a transition metal silicide. In particular, it is preferred that the etching mask film 52 be formed of a material formed of chromium or a chromium compound in which an element such as oxygen, nitrogen, or carbon is added to chromium. In this case, the etching mask film 52 may have an antireflection function and the transfer mask 60 may be produced under a state in which the etching mask film 52 remains on the light-shielding film 51.

[Method of Manufacturing Transfer Mask 60]

Figure 3:
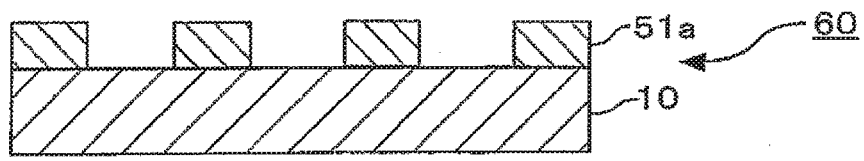
FIG. 3 is a schematic sectional view for illustrating exemplary structure of a transfer mask according to the embodiment of this invention.

This invention is the transfer mask 60 having a feature in that the transfer pattern is formed in the thin film of the mask blank 50. FIG. 3 is a schematic sectional view for illustrating exemplary structure of the transfer mask 60 according to this invention. The transfer mask 60 according to this invention may be produced through forming the transfer pattern in the thin film of the mask blank 50 produced by the method of manufacturing the mask blank 50 according to this invention. In the case illustrated in FIG. 3, the light-shielding film pattern 51*a* (transfer pattern) is formed on the main surface of the mask blank substrate 10. The transfer pattern may be formed in the thin film using a known method.

[Method of Manufacturing Semiconductor Device]

By transferring a transfer pattern such as a circuit pattern based on the transfer patter of the transfer mask 60 to a resist film formed on a transfer member such as a semiconductor substrate in a lithography process using the transfer mask 60 described above and a predetermined exposure apparatus, and by various other steps, a semiconductor device in which various patterns, such as wiring are formed on a semiconductor substrate may be produced.

A fiducial mark may be formed on the mask blank substrate 10 and the mask blank 50 described above, and positions of the fiducial mark and of a fatal defect detected by the above-mentioned highly sensitive defect inspection apparatus may be controlled based on coordinates thereof. On the basis of positional information of the fatal defect (defect data) obtained, by correcting drawing data when the transfer mask 60 is produced so that the light-shielding pattern 51*a* (transfer pattern) is formed at a location where the fatal defect exists based on the above-mentioned defect data and transferred pattern (circuit pattern) data, defects may be reduced.

EXAMPLE

Now, the embodiment of the present invention is described in more detail by way of Examples. Note that, the present invention is not limited to the following Examples.

Example 1

Manufacturing of Mask Blank Substrate 10

As the mask blank substrate 10 of Example 1, synthetic quartz glass sized to be 152.4 mm×152.4 mm and having a thickness of 6.35 mm was prepared, and the rough polishing step, the precision polishing step, and the ultra-precision polishing step were performed as follows.

(1) Rough Polishing Step

Ten synthetic quarts glass substrates subjected to an end surface chamfering treatment and a grinding treatment using a double side lapping apparatus were set in a double side polisher, and the rough polishing step was performed under the following polishing conditions. A treatment load and polishing time were appropriately adjusted.

Polishing liquid: cerium oxide (mean particle size of from 2 µm to 3 µm)+water

Polishing pad: hard polisher (urethane pad)

After the rough polishing step, in order to remove abrasive grains attached to the glass substrate, the glass substrate was immersed in a cleaning bath (ultrasound application) to be cleaned.

(2) Precision Polishing Step

Using the double side polisher described above, the precision polishing step was performed with regard to the ten glass substrates after the rough polishing step, under the following polishing conditions. A treatment load and polishing time were appropriately adjusted.

Polishing liquid: cerium oxide (mean particle size of 1 µm)+water

Polishing pad: soft polisher (urethane pad)

After the precision polishing step, in order to remove abrasive grains attached to the glass substrate, the glass substrate was immersed in a cleaning bath (ultrasound application) to be cleaned.

(3) Ultra-precision Polishing Step

Using the double side polisher described above, the ultra-precision polishing step was performed with regard to the ten glass substrates after the ultra-precision polishing step, under the following polishing conditions. A treatment load and polishing time were appropriately adjusted.

Polishing liquid: polishing liquid containing water, colloidal silica (mean particle size D50: 18 nm), and additive (hydroxyethylcellulose and alkaline compound [ammonia]) with a pH of 10.5

Polishing pad 17: polishing pad 17 having a pad structure of PET (base material 17A)/nap layer 17B, a compression deformation amount of 274 µm, and a 100% modulus of the nap layer 17B of 3.0 MPa was used.

The base material 17A of the polishing pad 17 was a PET resin film, and the nap layer 17B was formed of a polyurethane resin. Further, the compression deformation amount of the polishing pad 17 and the 100% modulus of the nap layer 17B were measured by the methods described above. After the ultra-precision polishing step, in order to remove abrasive grains (colloidal silica) attached to the glass substrate, after cleaning with a low concentration aqueous solution of hydrofluosilicic acid, rinsing was performed with pure water.

In this way, the mask blank substrate 10 of Example 1 was produced.

<Power Spectrum Analysis of Mask Blank Substrate 10>

Figure 4:
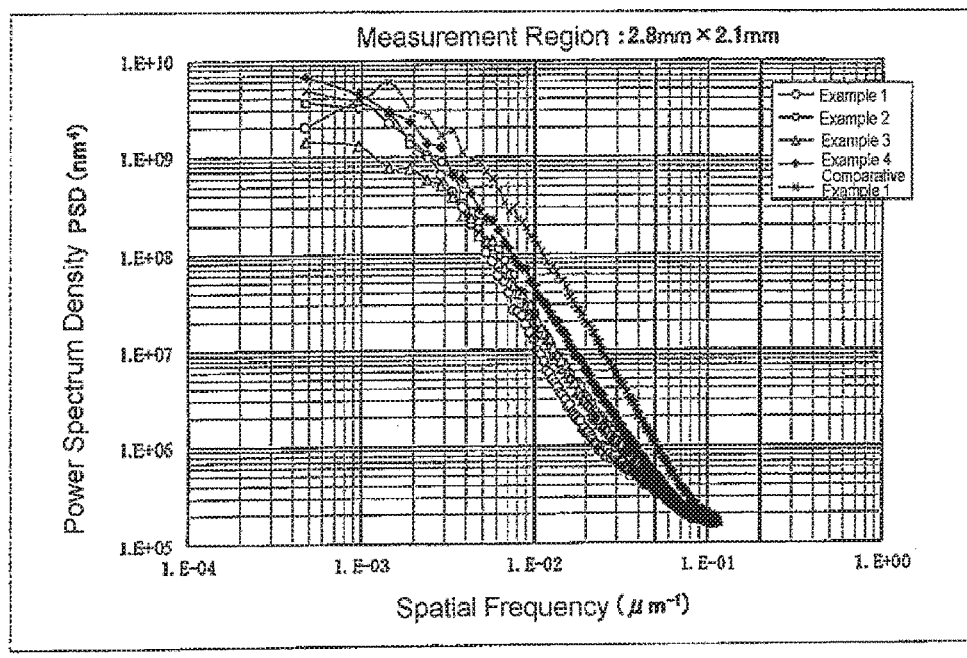
FIG. 4 is a graph for showing the result of measurement of power spectrum density in a region of 2.8 mm×2.1 mm on a main surface of each of substrates for mask blanks of Examples 1 to 4 and Comparative Example 1 using a white light interferometer with a pixel number of 640×480.
Figure 5:
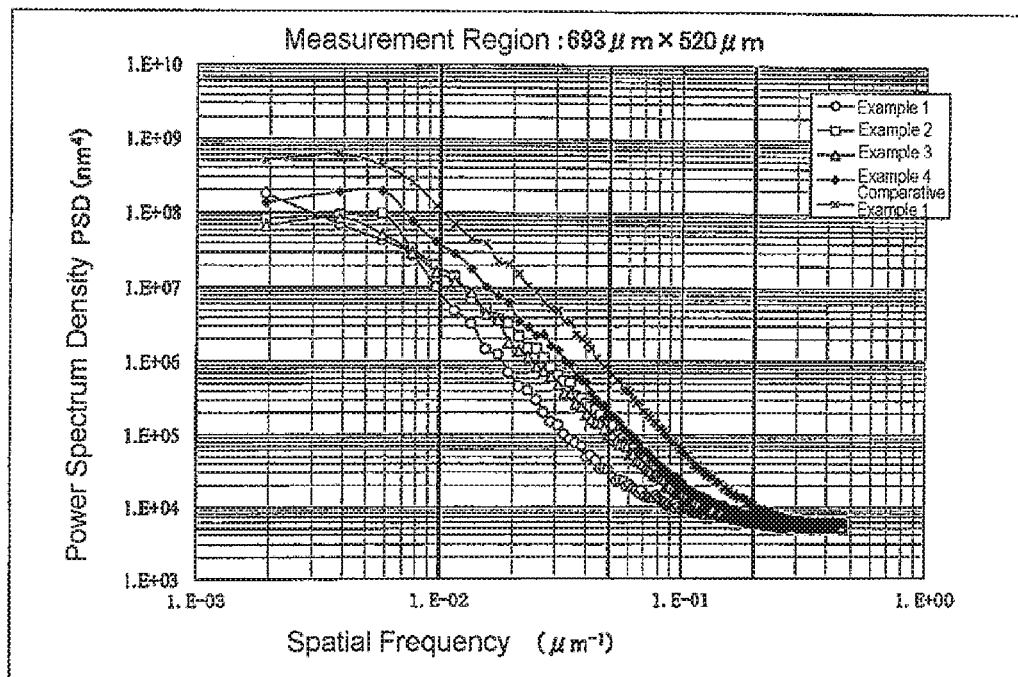
FIG. 5 is a graph for showing the result of measurement of power spectrum density in a region of 693 μm×520 μm on the main surface of each of the substrates for mask blanks of Examples 1 to 4 and Comparative Example 1 using a white light interferometer with a pixel number of 640×480.
Figure 6:
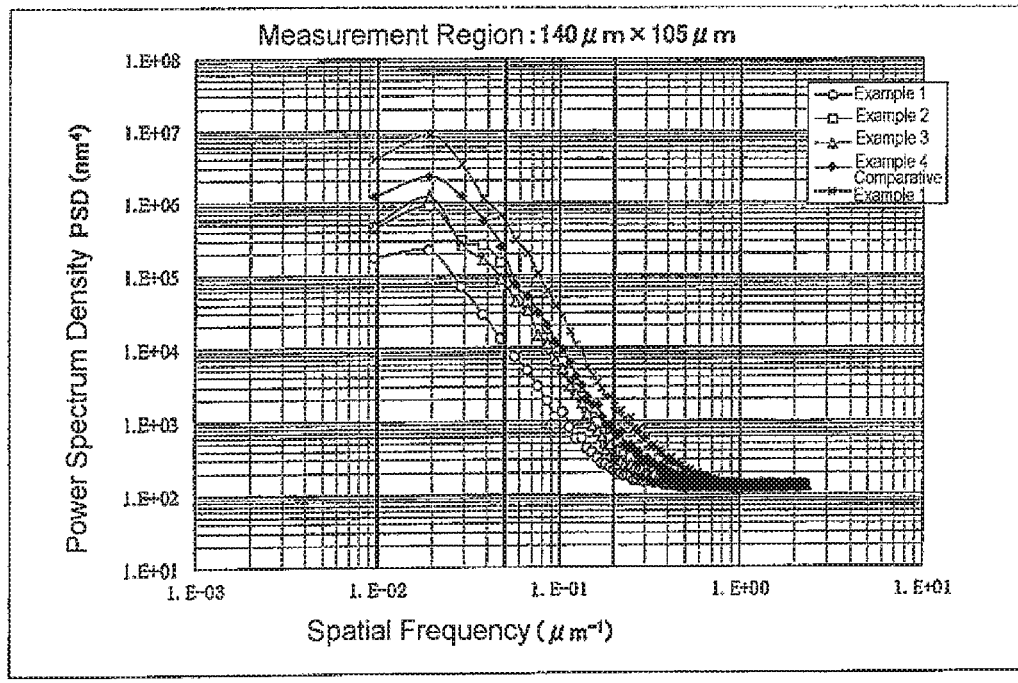
FIG. 6 is a graph for showing the result of measurement of power spectrum density in a region of 140 μm×105 μm on the main surface of each of the substrates for mask blanks of Examples 1 to 4 and Comparative Example 1 using a white light interferometer with a pixel number of 640×480.

The surface state of the mask blank substrate 10 of Example 1 was measured with a noncontact surface profile measuring machine NewView 7300 produced by Zygo Corporation, which is a white light interferometer, and power spectrum analysis was performed. Power spectrum analysis was performed with regard to a measurement region of 2.8 mm×2.1 mm measured using the white light interferometer, with a pixel number of 640×480. The result is shown in FIG. 4. Similarly, the result of power spectrum analysis with regard to a measurement region of 693 µm×520 µm (pixel number of 640×480) is shown in FIG. 5, and the result of power spectrum analysis with regard to a measurement region of 140 µm×105 µm (pixel number of 640×480) is shown in FIG. 6. In FIG. 4 to FIG. 6, the thick lines designating spatial frequency values designate spatial frequencies of $1.0 \times 10^{-2}$ µm$^{-1}$, $5.0 \times 10^{-2}$ µm$^{-1}$, and $2.0 \times 10^{-1}$ µm$^{-1}$, respectively, from the left.

As shown in FIG. 4, the result of the power spectrum analysis of the mask blank substrate 10 of Example 1 was that the power spectrum density at the spatial frequency of $1.0 \times 10^{-2}$ µm$^{-1}$ was $1.3 \times 10^{7}$ nm$^{4}$, which was lower than $6.0 \times 10^{7}$ nm$^{4}$.

As shown in FIG. 5, the result of the power spectrum analysis of the mask blank substrate 10 of Example 1 was that the power spectrum density at the spatial frequency of $5.0 \times 10^{-2}$ $\mu m^{-1}$ was $3.2 \times 10^4$ $nm^4$, which was lower than $3.0 \times 10^5$ $nm^4$ (FIG. 5).

As shown in FIG. 6, the result of the power spectrum analysis of the mask blank substrate 10 of Example 1 was that the power spectrum density at the spatial frequency of $2.0 \times 10^{-1}$ $\mu m^{-1}$ was $2.1 \times 10^2$ $nm^4$, which was lower than $8.0 \times 10^2$ $nm^4$.

<Defect Inspection>

Defect inspection of a region of 132 mm×132 mm of the main surface of the mask blank substrate 10 of Example 1 produced as described above was made using a defect inspection apparatus ("MAGICS M1320" produced by Lasertec Corporation) of the two beam interference method (inspection light source wavelength of 488 nm). Inspection sensibility conditions of the defect inspection apparatus were set such that polystyrene latex (PSL) particles having a diameter of 150 nm dispersed on a main surface of a glass substrate were able to be detected. The PSL particles have such characteristics that the probability that the distance between the particles was 1 mm or less was 1% or less. Further, using the defect inspection apparatus of the two beam interference method, the substrate was rotated by 90°, and defect inspection of a region of 132 mm×132 mm of the main surface of the mask blank substrate 10 produced as described above was made. The first defect inspection is herein referred to as "defect inspection at 0°" and the defect inspection with the substrate being rotated by 90° is herein referred to as "defect inspection at 90°". Through comparing the result of the defect inspection at 0° and the result of the defect inspection at 90°, whether a defect was a false defect or a real defect was distinguished.

When the mask blank substrate 10 of Example 1 was measured using the defect inspection apparatus of the two beam interference method, the number of detected real defects was one and the number of detected false defects was six in the defect inspection at 0°. Further, the number of detected real defects was two and the number of detected false defects was one in the defect inspection at 90°.

Next, defect inspection of a region of 132 mm×132 mm of the main surface of the mask blank substrate 10 of Example 1 produced as described above was made using a defect inspection apparatus ("MAGICS M1350" produced by Lasertec Corporation) of the spatial filter method (inspection light source wavelength of 488 nm). Inspection sensibility conditions of the defect inspection apparatus were set such that polystyrene latex (PSL) particles having a diameter of 60 nm dispersed on a main surface of a glass substrate were able to be detected. A method of distinguishing whether a detected defect was a false defect or a real defect was similar to that in the case of the defect inspection apparatus of the two beam interference method. As a result, the number of detected real defects was six and the number of detected false defects was 55 when the mask blank substrate 10 of Example 1 was measured using the defect inspection apparatus of the spatial filter method.

Example 2

Manufacturing of Mask Blank Substrate 10

As the mask blank substrate 10 of Example 2, as in Example 1, synthetic quartz glass sized to be 152.4 mm×152.4 mm and having a thickness of 6.35 mm was prepared, and the rough polishing step, the precision polishing step, and the ultra-precision polishing step were performed. However, conditions of the ultra-precision polishing step for the mask blank substrate 10 of Example 2 were as follows.

With regard to the mask blank substrate 10 of Example 2, the ultra-precision polishing step was performed as follows. That is, using the double side polisher described above, the ultra-precision polishing step was performed with regard to the ten glass substrates after the precision polishing step, under the following polishing conditions. A treatment load and polishing time were appropriately adjusted.

Polishing liquid: polishing liquid containing water, colloidal silica (mean particle size D50: 20 nm), and additive (hydroxyethylcellulose and alkaline compound [ammonia]) with a pH of 10.5.

The polishing pad 17 of Example 1 was used. After the ultra-precision polishing step, in order to remove abrasive grains (colloidal silica) attached to the glass substrate, after cleaning with a low concentration aqueous solution of hydrofluosilicic acid, rinsing was performed with pure water.

<Power Spectrum Analysis of Mask Blank Substrate 10>

As in Example 1, the surface state of the glass substrate of the mask blank substrate 10 of Example 2 was measured with a white light interferometer, and power spectrum analysis was performed. Power spectrum analysis was performed with regard to a measurement region of 2.8 mm×2.1 mm measured using the white light interferometer, with a pixel number of 640×480. The result is shown in FIG. 4. Similarly, the result of power spectrum analysis with regard to a measurement region of 693 μm×520 μm (pixel number of 640×480) is shown in FIG. 5, and the result of power spectrum analysis with regard to a measurement region of 140 μm×105 μm (pixel number of 640×480) is shown in FIG. 6.

As shown in FIG. 4, the result of the power spectrum analysis of the mask blank substrate 10 of Example 2 was that the power spectrum density at the spatial frequency of $1.0 \times 10^{-2}$ $\mu m^{-1}$ was $2.4 \times 10^7$ $nm^4$, which was lower than $6.0 \times 10^7$ $nm^4$.

As shown in FIG. 5, the result of the power spectrum analysis of the mask blank substrate 10 of Example 2 was that the power spectrum density at the spatial frequency of $5.0 \times 10^{-2}$ $\mu m^{-1}$ was $1.4 \times 10^5$ $nm^4$, which was lower than $3.0 \times 10^5$ $nm^4$.

As shown in FIG. 6, the result of the power spectrum analysis of the mask blank substrate 10 of Example 2 was that the power spectrum density at the spatial frequency of $2.0 \times 10^{-1}$ $\mu m^{-1}$ was $3.9 \times 10^2$ $nm^4$, which was lower than $8.0 \times 10^2$ $nm^4$.

<Defect Inspection>

As in Example 1, defect inspection of a region of 132 mm×132 mm of the main surface of the mask blank substrate 10 of Example 2 produced as described above was made using the defect inspection apparatus ("MAGICS M1320" produced by Lasertec Corporation) of the two beam interference method (inspection light source wavelength of 488 nm). When the mask blank substrate 10 of Example 2 was measured using the defect inspection apparatus of the two beam interference method, the number of detected real defects was zero and the number of detected false defects was nine in the defect inspection at 0°. Further, the number of detected real defects was zero and the number of detected false defects was 16 in the defect inspection at 90°.

Next, as in Example 1, defect inspection of a region of 132 mm×132 mm of the main surface of the mask blank substrate 10 of Example 2 produced as described above was made using the defect inspection apparatus ("MAGICS M1350" produced by Lasertec Corporation) of the spatial filter method (inspection light source wavelength of 488 nm). As a result, the number of detected real defects was zero and the number of detected false defects was 59 when the mask blank substrate 10 of Example 2 was measured using the defect inspection apparatus of the spatial filter method.

Example 3

Manufacturing of Mask Blank Substrate 10

As the mask blank substrate 10 of Example 3, as in Example 1, synthetic quartz glass sized to be 152.4 mm×152.4 mm and having a thickness of 6.35 mm was prepared, and the rough polishing step, the precision polishing step, and the ultra-precision polishing step were performed. However, conditions of the ultra-precision polishing step for the mask blank substrate 10 of Example 3 were as follows.

With regard to the mask blank substrate 10 of Example 3, the ultra-precision polishing step was performed as follows. That is, using the double side polisher described above, the ultra-precision polishing step was performed with regard to the ten glass substrates after the precision polishing step, under the following polishing conditions. A treatment load and polishing time were appropriately adjusted.

Polishing liquid: polishing liquid containing water, colloidal silica (mean particle size D50: 23 nm), and additive (hydroxyethylcellulose and alkaline compound [ammonia]) with a pH of 10.5

The polishing pad 17 of Example 1 was used. After the ultra-precision polishing step, in order to remove abrasive grains (colloidal silica) attached to the glass substrate, after cleaning with a low concentration aqueous solution of hydrofluosilicic acid, rinsing was performed with pure water.

<Power Spectrum Analysis of Mask Blank Substrate 10>

As in Example 1, the surface state of the glass substrate of the mask blank substrate 10 of Example 3 was measured with a white light interferometer, and power spectrum analysis was performed. Power spectrum analysis was performed with regard to a measurement region of 2.8 mm×2.1 mm measured using the white light interferometer, with a pixel number of 640×480. The result is shown in FIG. 4. Similarly, the result of power spectrum analysis with regard to a measurement region of 693 μm×520 μm (pixel number of 640×480) is shown in FIG. 5, and the result of power spectrum analysis with regard to a measurement region of 140 μm×105 μm (pixel number of 640×480) is shown in FIG. 6.

As shown in FIG. 4, the result of the power spectrum analysis of the mask blank substrate 10 of Example 3 was that the power spectrum density at the spatial frequency of $1.0 \times 10^{-2}$ μm$^{-1}$ was $2.3 \times 10^7$ nm$^4$, which was lower than $6.0 \times 10^7$ nm$^4$.

As shown in FIG. 5, the result of the power spectrum analysis of the mask blank substrate 10 of Example 3 was that the power spectrum density at the spatial frequency of $5.0 \times 10^{-2}$ μm$^{-1}$ was $1.0 \times 10^5$ nm$^4$, which was lower than $3.0 \times 10^5$ nm$^4$ (FIG. 5).

As shown in FIG. 6, the result of the power spectrum analysis of the mask blank substrate 10 of Example 3 was that the power spectrum density at the spatial frequency of $2.0 \times 10^{-1}$ μm$^{-1}$ was $3.4 \times 10^2$ nm$^4$, which was lower than $8.0 \times 10^2$ nm$^4$.

<Defect Inspection>

As in Example 1, defect inspection of a region of 132 mm×132 mm of the main surface of the mask blank substrate 10 of Example 3 produced as described above was made using the defect inspection apparatus ("MAGICS M1320" produced by Lasertec Corporation) of the two beam interference method (inspection light source wavelength of 488 nm). When the mask blank substrate 10 of Example 3 was measured using the defect inspection apparatus of the two beam interference method, the number of detected real defects was zero and the number of detected false defects was eight in the defect inspection at 0°. Further, the number of detected real defects was zero and the number of detected false defects was 11 in the defect inspection at 90°.

Next, as in example 1, defect inspection of a region of 132 mm×132 mm of the main surface of the mask blank substrate 10 of Example 3 produced as described above was made using the defect inspection apparatus ("MAGICS M1350" produced by Lasertec Corporation) of the spatial filter method (inspection light source wavelength of 488 nm). As a result, the number of detected real defects was five and the number of detected false defects was 53 when the mask blank substrate 10 of Example 3 was measured using the defect inspection apparatus of the spatial filter method.

Example 4

Manufacturing of Mask Blank Substrate 10

As the mask blank substrate 10 of Example 4, as in Example 1, synthetic quartz glass sized to be 152.4 mm×152.4 mm and having a thickness of 6.35 mm was prepared, and the rough polishing step, the precision polishing step, and the ultra-precision polishing step were performed. However, conditions of the ultra-precision polishing step for the mask blank substrate 10 of Example 4 were as follows.

With regard to the mask blank substrate 10 of Example 4, the ultra-precision polishing step was performed as follows. That is, using the double side polisher described above, the ultra-precision polishing step was performed with regard to the ten glass substrates after the precision polishing step, under the following polishing conditions. A treatment load and polishing time were appropriately adjusted.

Polishing liquid: polishing liquid containing water, colloidal silica (mean particle size D50: 80 nm), and additive (hydroxyethylcellulose and alkaline compound [ammonia]) with a pH of 10.5

The polishing pad 17 of Example 1 was used. After the ultra-precision polishing step, in order to remove abrasive grains (colloidal silica) attached to the glass substrate, after cleaning with a low concentration aqueous solution of hydrofluosilicic acid, rinsing was performed with pure water.

<Power Spectrum Analysis of Mask Blank Substrate 10>

As in Example 1, the surface state of the glass substrate of the mask blank substrate 10 of Example 4 was measured with a white light interferometer, and power spectrum analysis was performed. Power spectrum analysis was performed with regard to a measurement region of 2.8 mm×2.1 mm measured using the white light interferometer, with a pixel number of 640×480. The result is shown in FIG. 4. Similarly, the result of power spectrum analysis with regard to a measurement region of 693 μm×520 μm (pixel number of 640×480) is shown in FIG. 5, and the result of power spectrum analysis with regard to a measurement region of 140 µm×105 µm (pixel number of 640×480) is shown in FIG. 6.

As shown in FIG. 4, the result of the power spectrum analysis of the mask blank substrate 10 of Example 4 was that the power spectrum density at the spatial frequency of $1.0\times10^{-2}$ µm$^{-1}$ was $4.6\times10^7$ nm$^4$, which was lower than $6.0\times10^7$ nm$^4$.

As shown in FIG. 5, the result of the power spectrum analysis of the mask blank substrate 10 of Example 4 was that the power spectrum density at the spatial frequency of $5.0\times10^{-2}$ µm$^{-1}$ was $2.0\times10^5$ nm$^4$, which was lower than $3.0\times10^5$ nm$^4$.

As shown in FIG. 6, the result of the power spectrum analysis of the mask blank substrate 10 of Example 4 was that the power spectrum density at the spatial frequency of $2.0\times10^{-1}$ µm$^{-1}$ was $7.2\times10^2$ nm$^4$, which was lower than $8.0\times10^2$ nm$^4$.

<Defect Inspection>

As in Example 1, defect inspection of a region of 132 mm×132 mm of the main surface of the mask blank substrate 10 of Example 4 produced as described above was made using the defect inspection apparatus ("MAGICS M1320" produced by Lasertec Corporation) of the two beam interference method (inspection light source wavelength of 488 nm). When the mask blank substrate 10 of Example 4 was measured using the defect inspection apparatus of the two beam interference method, the number of detected real defects was zero and the number of detected false defects was 27 in the defect inspection at 0°. Further, the number of detected real defects was one and the number of detected false defects was 34 in the defect inspection at 90°.

Next, as in Example 1, defect inspection of a region of 132 mm×132 mm of the main surface of the mask blank substrate 10 of Example 4 produced as described above was made using the defect inspection apparatus ("MAGICS M1350" produced by Lasertec Corporation) of the spatial filter method (inspection light source wavelength of 488 nm). As a result, the number of detected real defects was one and the number of detected false defects was 114 when the mask blank substrate 10 of Example 4 was measured using the defect inspection apparatus of the spatial filter method.

Comparative Example 1

Manufacturing of Mask Blank Substrate 10

As the mask blank substrate 10 of Comparative Example 1, as in Example 1, synthetic quartz glass sized to be 152.4 mm×152.4 mm and having a thickness of 6.35 mm was prepared, and the rough polishing step, the precision polishing step, and the ultra-precision polishing step were performed. However, conditions of the ultra-precision polishing step for the mask blank substrate 10 of Comparative Example 1 were as follows.

With regard to the mask blank substrate 10 of Comparative Example 1, the ultra-precision polishing step was performed as follows. That is, using the double side polisher described above, the ultra-precision polishing step was performed with regard to the ten glass substrates after the precision polishing step, under the following polishing conditions. A treatment load and polishing time were appropriately adjusted.

Polishing liquid: polishing liquid containing water and colloidal silica (mean particle size D50: 110 nm), with a pH of 10.5

The polishing pad 17 of Example 1 was used. After the ultra-precision polishing step, in order to remove abrasive grains (colloidal silica) attached to the glass substrate, after cleaning with a low concentration aqueous solution of hydrofluosilicic acid, rinsing was performed with pure water.

<Power Spectrum Analysis of Mask Blank Substrate 10>

As in Example 1, the surface state of the glass substrate of the mask blank substrate 10 of Comparative Example 1 was measured with a white light interferometer, and power spectrum analysis was performed. Power spectrum analysis was performed with regard to a measurement region of 2.8 mm×2.1 mm measured using the white light interferometer, with a pixel number of 640×480. The result is shown in FIG. 4. Similarly, the result of power spectrum analysis with regard to a measurement region of 693 µm×520 µm (pixel number of 640×480) is shown in FIG. 5, and the result of power spectrum analysis with regard to a measurement region of 140 µm×105 µm (pixel number of 640×480) is shown in FIG. 6.

As shown in FIG. 4, the result of the power spectrum analysis of the mask blank substrate 10 of Comparative Example 1 was that the power spectrum density at the spatial frequency of $1.0\times10^{-2}$ µm$^{-1}$ was $1.4\times10^8$ nm$^4$, which was higher than $6.0\times10^7$ nm$^4$.

As shown in FIG. 5, the result of the power spectrum analysis of the mask blank substrate 10 of Comparative Example 1 was that the power spectrum density at the spatial frequency of $5.0\times10^{-2}$ µm$^{-1}$ was $8.1\times10^5$ nm$^4$, which was higher than $3.0\times10^5$ nm$^4$.

As shown in FIG. 6, the result of the power spectrum analysis of the mask blank substrate 10 of Comparative Example 1 was that the power spectrum density at the spatial frequency of $2.0\times10^{-1}$ µm$^{-1}$ was $1.6\times10^3$ nm$^4$, which was higher than $8.0\times10^2$ nm$^4$.

<Defect Inspection>

As in Example 1, defect inspection of a region of 132 mm×132 mm of the main surface of the mask blank substrate 10 of Comparative Example 1 produced as described above was made using the defect inspection apparatus ("MAGICS M1320" produced by Lasertec Corporation) of the two beam interference method (inspection light source wavelength of 488 nm). When the mask blank substrate 10 of Comparative Example 1 was measured using the defect inspection apparatus of the two beam interference method, the number of detected real defects was two and the number of detected false defects was 1,317 in the defect inspection at 0°. Further, the number of detected real defects was two and the number of detected false defects was 1,067 in the defect inspection at 90°.

Next, as in Example 1, defect inspection of a region of 132 mm×132 mm of the main surface of the mask blank substrate 10 of Comparative Example 1 produced as described above was made using the defect inspection apparatus ("MAGICS M1350" produced by Lasertec Corporation) of the spatial filter method (inspection light source wavelength of 488 nm). As a result, the number of detected real defects was five and the number of detected false defects was 300 when the mask blank substrate 10 of Comparative Example 1 was measured using the defect inspection apparatus of the spatial filter method.

As described above, in the defect inspection using the defect inspection apparatus of the two beam interference method, with regard to the mask blank substrate 10 of Comparative Example 1 without the predetermined spatial frequency by the power spectrum analysis, the number of detected false defects was 1,317 (at 0°) and 1,067 (at 90°), which were orders of magnitude larger than those of the mask blank substrates 10 of Examples 1 to 4. On the other hand, in the cases of the mask blank substrates 10 of Examples 1 to 4 with the predetermined spatial frequency by the power spectrum analysis, the number of detected false defects was 34 at the maximum (Example 4, at 90°). Therefore, it was made clear that, in the case of the mask blank substrate 10 with the predetermined spatial frequency by the power spectrum analysis, remarkable difference may be suppressed from being made in the number of detected false defects among substrates.

The number of detected false defects of Comparative Example 1 when the defect inspection apparatus of the spatial filter method was used was about six times, at the maximum, as much as those of Examples 1 to 4. Therefore, it was made clear that, when the defect inspection apparatus of the spatial filter method is used, difference in number of detected false defects between Examples 1 to 4 and Comparative Example 1 is relatively small compared with that when the defect inspection apparatus of the two beam interference method is used.

[Manufacturing of Mask Blank 50]

The surface profile of the main surface on the side on which the thin film was formed (one main surface) of each of the mask blank substrates 10 of Examples 1 to 4 and Comparative Example 1 produced as described above was measured using a surface profile analysis apparatus (Ultra-FLAT 200M (produced by Corning Tropel Corporation)) (the measurement region was a region inside a square of 142 mm×142 mm with reference to the center of the mask blank substrate 10, and the measurement region of the surface profile measured using the surface profile analysis apparatus is hereinafter the same). With regard to every mask blank substrate 10, the flatness in the region inside the square of 142 mm×142 mm of the main surface on the side on which the thin film was formed (one main surface) was 0.2 µm or less, and the surface profile was projecting.

Next, the light-shielding film 51 was formed on the main surface (one main surface) of each of the mask blank substrates 10 of Examples 1 to 4 and Comparative Example 1. Specifically, a MoSiN film was formed on the mask blank substrate 10 at a thickness of 47 nm as a lower layer of the light-shielding film 51, with a mixture target of molybdenum (Mo) and silicon (Si) (atom percent ratio of Mo:Si=13:87) being used as a sputtering target, by reactive sputtering (DC sputtering) using a single-wafer sputtering apparatus in a mixture gas atmosphere of argon and nitrogen (gas pressure of 0.1 Pa and gas flow rate ratio of Ar:$N_2$=51:49) with power of a DC power supply of 1.9 kW. Then, a MoSiN film was formed at a thickness of 13 nm as an upper layer of the light-shielding film 51, with the same mixture target of molybdenum (Mo) and silicon (Si) being used, by reactive sputtering (DC sputtering) in a mixture gas atmosphere of argon, nitrogen, and helium (gas pressure of 0.1 Pa and gas flow rate ratio of Ar:$N_2$:He=33:56:11) with power of a DC power supply of 1.9 kW.

Through the steps described above, the light-shielding film 51 for an ArF excimer laser (wavelength of 193 nm) having a lamination structure of the lower layer of MoSiN and the upper layer of MoSiN was formed on each of the mask blank substrates 10 of Examples 1 to 4 and Comparative Example 1 to obtain the substrates with a thin film of Examples 1 to 4 and Comparative Example 1. The light-shielding film 51 had an optical density of 3.0 or more for exposure light of the ArF excimer laser.

Then, the etching mask film 52 made of a chromium-based material (CrN film at a thickness of 5 nm) was formed on the light-shielding film 51 (thin film) of the substrates with a thin film of Examples 1 to 4 and Comparative Example 1 to produce the mask blank 50 in which the light-shielding film 51 and the etching mask film 52 were laminated on the glass substrate main surface. In this way, the mask blanks 50 of Examples 1 to 4 and Comparative Example 1 were able to be obtained.

[Manufacturing of Transfer Mask 60]

The resist film was formed on the etching mask film 52 of the mask blanks 50 of Examples 1 to 4 and Comparative Example 1 by spin coating. Then, a predetermined mask pattern was drawn on the resist film by exposure, and a developing process and the like were performed to form a resist pattern. Dry etching was performed using a mixture gas of $Cl_2$ and $O_2$ as an etching gas with the resist pattern being used as a mask, thereby forming a predetermined patter in the etching mask film 52.

Then, the resist film was separated, and dry etching was performed using a mixture gas of $SF_6$ and He as an etching gas with the etching mask film 52 having the predetermined mask pattern formed therein being used as a mask, thereby forming the predetermined mask pattern in the light-shielding film 51. Further, dry etching was performed using a mixture gas of $Cl_2$ and $O_2$ as an etching gas to remove the etching mask film 52. Through these steps, the transfer masks 60 of Examples 1 to 4 and Comparative Example 1 were produced each having the light-shielding film pattern 51a where the predetermined mask pattern is formed on the glass substrate main surface.

[Manufacturing of Semiconductor Device]

Then, with regard to each of the transfer masks 60 of Examples 1 to 4 and Comparative Example 1 described above, simulation of a transferred image, which is transferred onto the resist film on a semiconductor device through exposure to light having a wavelength of 193 nm was performed using AIMS 193 (produced by Carl Zeiss AG). The transferred image through light exposure of the simulation with regard to each of the transfer masks 60 of Examples 1 to 4 was examined, and it was found that the design specifications were satisfactorily satisfied. From these results, it may be said that, even if each of the transfer masks 60 of Examples 1 to 4 is set on a mask stage of an exposure apparatus and an image is transferred onto the resist film on the semiconductor device through light exposure, a circuit pattern finally formed on the semiconductor device is formed with high precision.

On the other hand, a transferred image through light exposure of the simulation with regard to the transfer mask 60 of Comparative Example 1 was examined, and unsatisfactory transfer was confirmed at a plurality of places. This is because, in defect inspection of the mask blank substrate 10, the mask blank 50, and the transfer mask 60, fatal defects among false defects were not able to be detected and appropriate correction to image drawing and correction to the mask were not made, and thus, the fatal defects existed on the transfer mask 60. From this result, it may be said that, when the transfer mask 60 of Comparative Example 1 is set on a mask stage of an exposure apparatus and an image is transferred onto the resist film on the semiconductor device, a circuit pattern finally formed on the semiconductor device includes defects.

This invention has been described by means of preferred embodiments so far. However, it goes without saying that this invention is not limited to those embodiments and various modifications may be made thereto without departing from the gist of this invention, and those modifications are encompassed in the scope of this invention as well.

This application claims the benefit of priority based on Japanese Patent Application No. 2014-63308, filed on Mar. 26, 2014, and the entire disclosure of which is incorporated as a reference document herein.

REFERENCE SIGNS LIST 10 mask blank substrate (substrate)
12 sun gear
13 internal gear
14 carrier
15 upper surface plate
16 lower surface plate
17 polishing pad
17A base material
17B nap layer
18 pore
50 mask blank (transmission type mask blank)
51 light-shielding film
51a light-shielding film pattern
52 etching mask film
60 transfer mask (transmission type mask)

The invention claimed is:

1. A mask blank substrate, comprising a substrate having two main surfaces, wherein one of the two main surfaces of the mask blank substrate, on a side on which a transfer pattern is formed, has such a surface profile that, when a measurement region of 2.8 mm×2.1 mm of the main surface in a transfer pattern formation region is measured using a white light interferometer under conditions of a pixel number of 640×480, a power spectrum density at a spatial frequency of $1.0\times10^{-2}$ $\mu m^{-1}$ calculated from a result of the measurement is $6.0\times10^7$ $nm^4$ or less.

2. A mask blank substrate according to claim 1, wherein the main surface on the side on which the transfer pattern is formed has such a surface profile that, when a measurement region of 693 μm×520 μm of the main surface in the transfer pattern formation region is measured using the white light interferometer under conditions of a pixel number of 640×480, a power spectrum density at a spatial frequency of $5.0\times10^{-2}$ $\mu m^{-1}$ calculated from a result of the measurement is $3.0\times10^5$ $nm^4$ or less.

3. A mask blank substrate according to claim 1, wherein the main surface on the side on which the transfer pattern is formed has a such surface profile that, when a measurement region of 140 μm×105 μm of the main surface in the transfer pattern formation region is measured using the white light interferometer under conditions of a pixel number of 640×480, a power spectrum density at a spatial frequency of $2.0\times10^{-1}$ $\mu m^{-1}$ calculated from a result of the measurement is $8.0\times10^2$ $nm^4$ or less.

4. A mask blank substrate according to claim 1, wherein the main surface on a side different from the side on which the transfer pattern is formed has such a surface profile that, when a measurement region of 2.8 mm×2.1 mm of the main surface in a region having the same size as the transfer pattern formation region is measured using the white light interferometer under conditions of a pixel number of 640×480, a power spectrum density at a spatial frequency of $1.0\times10^{-2}$ $\mu m^{-1}$ calculated from a result of the measurement is $6.0\times10^7$ $nm^4$ or less.

5. A mask blank, comprising a thin film for forming the transfer pattern formed on the main surface of the mask blank substrate of claim 1 on the side on which the transfer pattern is formed.

6. A transfer mask, comprising the thin film of the mask blank of claim 5, which has the transfer pattern formed thereon.

7. A method of manufacturing a mask blank substrate comprising a substrate having two main surfaces, the method comprising a defect inspection step of making defect inspection using a two beam interference method with regard to one of the two main surfaces of the mask blank substrate on a side on which a transfer pattern is formed and in a transfer pattern formation region,
wherein the main surface of the mask blank substrate on the side on which the transfer pattern is formed has such a surface profile that, when a measurement region of 2.8 mm×2.1 mm of the main surface in the transfer pattern formation region is measured using a white light interferometer under conditions of a pixel number of 640×480, a power spectrum density at a spatial frequency of $1.0\times10^{-2}$ $\mu m^{-1}$ calculated from a result of the measurement is $6.0\times10^7$ $nm^4$ or less.

8. A method of manufacturing a mask blank substrate according to claim 7, wherein the main surface of the mask blank substrate on the side on which the transfer pattern is formed has such a surface profile that, when a measurement region of 693 μm×520 μm of the main surface in the transfer pattern formation region is measured using the white light interferometer under conditions of a pixel number of 640×480, a power spectrum density at a spatial frequency of $5.0\times10^{-2}$ $\mu m^{-1}$ calculated from a result of the measurement is $3.0\times10^5$ $nm^4$ or less.

9. A method of manufacturing a mask blank substrate according to claim 7, wherein the main surface of the mask blank substrate on the side on which the transfer pattern is formed has such a surface profile that, when a measurement region of 140 μm×105 μm of the main surface in the transfer pattern formation region is measured using the white light interferometer under conditions of a pixel number of 640×480, a power spectrum density at a spatial frequency of $2.0\times10^{-1}$ $\mu m^{-1}$ calculated from a result of the measurement is $8.0\times10^2$ $nm^4$ or less.

10. A method of manufacturing a mask blank substrate according to claim 7, further comprising, before the defect inspection step, a polishing step of polishing the main surface of the mask blank substrate on the side on which the transfer pattern is formed through relatively moving the mask blank substrate on a polishing pad of a polishing surface plate while supplying a polishing liquid thereto.

11. A method of manufacturing a mask blank substrate according to claim 10, wherein the polishing liquid contains colloidal silica having a mean particle size D50 of 100 nm or less.

12. A method of manufacturing a mask blank, comprising a step of forming, on the main surface of the mask blank substrate, a thin film for forming a transfer pattern, on the side on which the transfer pattern is formed, the mask blank substrate being produced by the method of manufacturing a mask blank substrate of claim 7.

13. A method of manufacturing a transfer mask, comprising a step of forming the transfer pattern in the thin film of the mask blank produced by the method of manufacturing a mask blank of claim 12.

* * * * *